(12) United States Patent
Wright et al.

(10) Patent No.: US 8,796,292 B2
(45) Date of Patent: Aug. 5, 2014

(54) SELECTIVE ANTIBACTERIALS FOR CLOSTRIDIUM DIFFICILE INFECTIONS

(75) Inventors: George E. Wright, Worcester, MA (US); Wei-Chu Xu, Shrewsbury, MA (US)

(73) Assignee: GLSynthesis Inc., Worcester, MA (US)

( * ) Notice: Subject to any disclaimer, the term of this patent is extended or adjusted under 35 U.S.C. 154(b) by 0 days.

(21) Appl. No.: 13/395,296

(22) PCT Filed: Sep. 10, 2010

(86) PCT No.: PCT/US2010/048379
§ 371 (c)(1),
(2), (4) Date: May 3, 2012

(87) PCT Pub. No.: WO2011/031935
PCT Pub. Date: Mar. 17, 2011

(65) Prior Publication Data
US 2012/0232077 A1    Sep. 13, 2012

Related U.S. Application Data

(60) Provisional application No. 61/276,436, filed on Sep. 11, 2009.

(51) Int. Cl.
*A61K 31/522* (2006.01)
*C07D 473/18* (2006.01)

(52) U.S. Cl.
USPC ................................. 514/263.37; 544/276

(58) Field of Classification Search
USPC ........................................................ 544/277
See application file for complete search history.

(56) References Cited

U.S. PATENT DOCUMENTS

| | | | |
|---|---|---|---|
| 5,516,905 A | 5/1996 | Brown et al. | |
| 6,492,384 B1 | 12/2002 | Mederski et al. | |
| 6,926,763 B2 | 8/2005 | Wright et al. | |
| 2003/0181719 A1 | 9/2003 | Zhi et al. | |
| 2004/0014773 A1* | 1/2004 | Wright et al. | 514/261.1 |
| 2008/0113902 A1 | 5/2008 | Jabes et al. | |

FOREIGN PATENT DOCUMENTS

| | | |
|---|---|---|
| WO | WO-01/28561 A1 | 4/2001 |
| WO | WO-01/29010 A1 | 4/2001 |
| WO | WO-01/29045 A1 | 4/2001 |
| WO | WO-02/102792 A1 | 12/2002 |

OTHER PUBLICATIONS

Ali et al., "Design and Synthesis of Novel Antibacterial Agents with Inhibitory Activity against DNA Polymerase III," *Bioorg. Med. Chem. Lett.* 11: 2185-2188 (2001).
Braithwaite et al., "Compilation, alignment, and phylogenetic relationships of DNA polymerases," *Nucleic Acids Res.* 21: 787-802 (1993).
Brown et al., "Inhibitors of *Bacillus subtilis* DNA Polymerase III. 6-(Arylalkylamino)uracils and 6-Anilinouracils," *J. Med. Chem.* 20: 1186-1189 (1977).
Butler et al., "Development of novel inhibitor probes of DNA polymerase III based on dGTP analogs of the HPUra type: base, nucleoside and nucleotide derivatives of $N^2$-(3,4-dichlorobenzyl)guanine," *Nucl Acids Res.* 18: 7381-7387 (1990).
de Bode et al., "Deazapurine derivatives XII. Investigations on the synthesis of 3-deazaguanine," *Recl. Tray. Chim. Pays-Bas* 93: 3-6 (1974).
Earl et al., "The synthesis of 8-aza-3-deazaguanosine [6-amino-1-(β-D-ribofuranosyl)-*v*-triazolo[4,5-*c*]pyridin-4-one] via a novel 1,3-dipolar cycloaddition reaction," *Can. J. Chem.* 58: 2550-2561 (1980).
Hookman et al., "*Clostridium difficile* associated infection, diarrhea and colitis," *World J. Gastroenterol* 15: 1554-1580 (2009).
Mederski et al., "Non-peptide Angiotensin II Receptor Antagonists: Synthesis and Biological Activity of a Series of Novel 4, 5-Dihydro-4-oxo-3H-imidazo[4,5-c]pyridine Derivatives," *J. Med. Chem.* 37: 1632-1645 (1994).
Medveczky et al., "Haloanilino Derivatives of Pyrimidines, Purines, and Purine Nucleoside Analogs: Synthesis and Activity against Human Cytomegalovirus," *J. Med. Chem.* 38: 1811-1819 (1995).
Rousseau et al., "The Synthesis of Various Chloroimidazo[4,5-*c*]pyridines and Related Derivatives," *J. Heterocycl. Chem.* 2: 196-201 (1965).
Stimac et al., "The Synthesis of v-Triazolo[4,5-*c*]pyridine Nucleosides," *Nucleosides & Nucleotides* 10: 727-728 (1991).
Tarantino et al., "6-Anilinouracil-Based Inhibitors of *Bacillus subtilis* DNA Polymerase III: Antipolymerase and Antimicrobial Structure-Activity Relationships Based on Substitution at Uracil N3," *J. Med. Chem.* 42: 2035-2040 (1999).
Wright et al., "DNA polymerase III: A new target for antibiotic development," *Curr. Opin. Anti-Infect. Invest. Drugs*, 1: 45-48 (1999).
Wright et al., "Inhibition of *Bacillus subtilis* DNA Polymerase III by Arylhydrazinopyrimidines," *Biochim. Biophys. Acta.* 432: 37-48 (1976).
Wright et al., "Synthesis, Cell Growth Inhibition, and Antitumor Screening of 2-(*p-n*-Butylanilino)purines and Their Nucleoside Analogues," *J. Med. Chem.*, 30: 109-116 (1987).
Xu et al., "Synthesis, Properties, and Pharmacokinetic Studies of $N^2$-Phenylguanine Derivatives as Inhibitors of Herpes Simplex Virus Thymidine Kinases," *J. Med. Chem.* 38: 49-57 (1995).
International Search Report and Written Opinion of the International Searching Authority for International Application No. PCT/US2010/48379, mailed Oct. 22, 2010 (11 pages).
Wright et al., "Active site directed inhibitors of replication-specific bacterial DNA polymerases," Bioorg Med Chem Lett. 15(3):729-732 (2005).
Supplementary European Search Report for European Patent Application No. 10816135.7, dated Jun. 11, 2013 (5 pages).

* cited by examiner

*Primary Examiner* — Golam M M Shameem
*Assistant Examiner* — Laura Daniel
(74) *Attorney, Agent, or Firm* — Clark & Elbing LLP; Kristina Bieker-Brady

(57) ABSTRACT

The invention features compounds of formula (I): The compounds are useful as antibacterial agents, especially again *Clostridium difficile*-associated diseases.

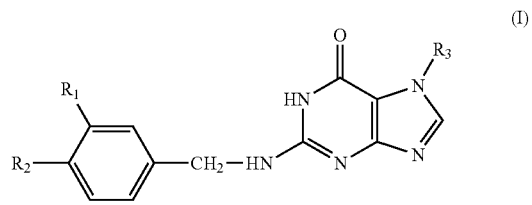

(I)

13 Claims, 9 Drawing Sheets

SELECTIVE ANTIBACTERIALS FOR CLOSTRIDIUM DIFFICILE INFECTIONS

STATEMENT AS TO FEDERALLY SPONSORED RESEARCH

The invention described herein was supported in whole or in part by SBIR grant number AI051103 from the National Institutes of Health. The government has certain rights in the invention.

CROSS-REFERENCE TO RELATED APPLICATIONS

This application claims benefit of U.S. Provisional Application No. 61/276,436, filed Sep. 11, 2009, which is hereby incorporated by reference.

TECHNICAL FIELD

This invention relates to antibacterial compounds that are selectively active against *Clostridium difficile* in vitro and in vivo, and more particularly to 7-substituted 2-benzylamino-6-oxopurines and salts thereof.

BACKGROUND

Bacterial pathogens pose a serious threat to public health. Two of the Gram-positive pathogens, *Staphylococcus aureus* and *Enterococcus fecalis/fecium*, are primarily nosocomial (hospital-acquired) pathogens; together, they presently account for the majority of nosocomial diseases. Gram-negative bacteria such as *Escherichia coli, Salmonella typhimurium*, and *Pseudomonas aeruginosa*, also cause significant diseases in humans. These organisms are aerobic bacteria, i.e., ones that grow in oxygen-containing atmospheres.

Important to health are "anaerobic" bacteria, i.e., those which grow in oxygen-depleted atmospheres, such as are found in intestinal milieu. Gram-positive anaerobes, such as Lactobacilli, Bifidobacteria, and Eubacteria, and Gram-negative anaerobes, such as Bacteroides, represent "good" intestinal organisms important to health, whereas the Gram-positive anaerobes *Clostridium difficile* and *Clostridium perfringens* represent pathogenic bacteria. *Clostridium difficile* (*C. diff*) has been increasingly associated with disease in human patients, ironically often as a result of treatment with certain antibiotic drugs. The most common disease is referred to as *C. diff*-associated diarrhea (CDAD).

SUMMARY OF THE INVENTION

In general, the invention is based on the unexpected discovery that certain 7-substituted-2-(benzylamino)-6-oxopurines have potent activity against the growth of the intestinal anaerobe *C. diff.*, but unexpectedly weak activity against other, intestinal Gram-positive anaerobes. The compounds can be administered to reduce the likelihood of developing or to treat *C. diff.* infections in human patients.

In one aspect, the invention features a compound having the formula:

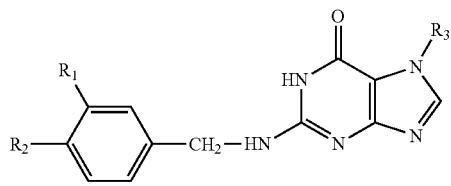

wherein $R^1$ and $R^2$ are, independently, H, halo, $C_{1-6}$ haloalkyl, or $C_{1-6}$ haloalkoxy;

wherein $R^3$ is $(CH_2)_m$-$\{(A)_o$-$(CH_2)_p\}_q$—B;

in which A is $CH_2$, $CH=CH$, $C\equiv C$, CO, O, S, $NR^6$, $CHR^7$, OC(O), (O)CO, $CONR^{10}$, $NR^{11}CO$, $SO_2NH$, $NHSO_2$, or $C_{3-8}$ cycloalkyl, wherein each $R^6$, $R^{10}$, and $R^{11}$ is, independently, H or $C_{1-6}$ alkyl; $R^7$ is OH or $C_{1-6}$ alkyl; and each of $R^8$ and $R^9$ is, independently, H, halo, or $C_{1-6}$ alkyl;

in which B is H, halo, substituted or unsubstituted $C_{1-10}$ alkyl, substituted or unsubstituted $C_{3-8}$ cycloalkyl, substituted or unsubstituted $C_{2-8}$ heterocyclyl or $C_{1-10}$ heteroaryl, $NH_2$, CN, $OR^{12}$, $SR^{13}$, $COR^{14}$, $OCOR^{15}$, $NR^{16}COR^{17}$, $NR^{18}R^{19}$, $NR^{20}CONHR^{21}$, CN, $CH(CO_2R^{22})_2$, $CO_2R^{23}$, $NHSO_2R^{24}$, $CONR^{25}R^{26}$, or $CH_2COR^{27}$, in which each of $R^{12}$-$R^{27}$ is, independently, H, substituted or unsubstituted $C_{1-6}$ alkyl, substituted or unsubstituted $C_{3-8}$ cycloalkyl, substituted or unsubstituted $C_{6-12}$ aryl, substituted or unsubstituted $C_{7-20}$ arylalkyl, substituted or unsubstituted $C_{7-20}$ alkylaryl, substituted or unsubstituted $C_{2-8}$ heterocyclyl or $C_{4-10}$ heteroaryl, substituted or unsubstituted $C_{1-3}$ acyl, or substituted or unsubstituted $C_{1-6}$ alkylsulfonyl;

m is 1-5, o is 0-4, p is 0-4, and q is 0-4;

or an optical isomer thereof, or a pharmaceutically acceptable salt thereof.

In certain embodiments, when $R^1$ and $R^2$ are chloro, $R^3$ is not 4-methoxybutyl, 4-(N-morpholinyl)butyl, 2-methoxyethyl, 5-methoxypentyl, 5-ethoxypentyl, 5-propoxypentyl, 5-methylthiopentyl, 4-hydroxybutyl, 4-acetoxybutyl, 4-bromobutyl, 4-iodobutyl, 4-(N-piperazinyl)butyl, 5-hydroxypentyl, 5-acetoxypentyl, or 5-iodopentyl.

In certain embodiments, $R^1$ and $R^2$ are, independently H, halo, trihalomethyl, trifluoroethyl, or trihalomethoxy. In particular, $R^1$ and $R^2$ can be selected, independently, from the group consisting of Cl, Br, I, $CF_3$, $OCF_3$, $CF_2CF_3$, and $CH_2CF_3$, e.g., both chloro. $R^3$ is, for example, 2-(N-morpholinyl)ethyl, 3-(N-morpholinyl)propyl, 5-(N-morpholinyl)pentyl, 2-[(N-morpholinyl)ethoxy]ethyl, 2-[(N-morpholinyl)-methyl]cyclobutylmethyl, or 2-[(N-morpholinyl)methyl]cyclopentylmethyl. In other examples, $R^3$ is selected from the group consisting of ω-(N-aziridinyl)-$C_{1-10}$ alkyl, ω-(N-pyrrolidinyl)-$C_{1-10}$ alkyl, ω-(N-piperidinyl)-$C_{1-10}$ alkyl, and ω-(N-piperazinyl)-$C_{1-10}$ alkyl.

Exemplary compounds have one of the formulas:

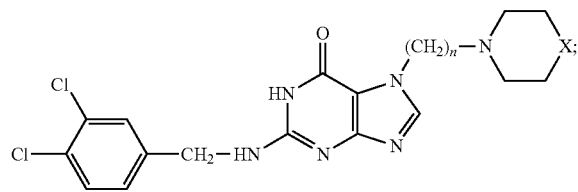

n = 2-5; X = CH$_2$, NH, O

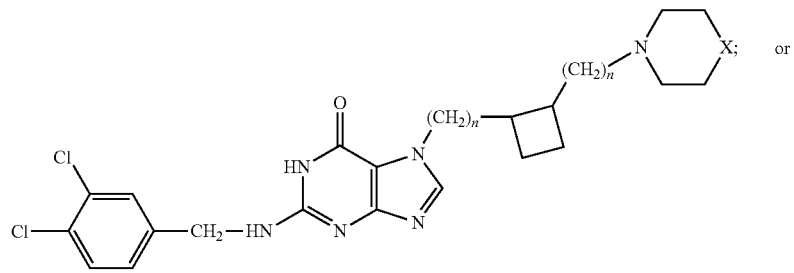

n = 1 or 2; X = CH$_2$, NH, O

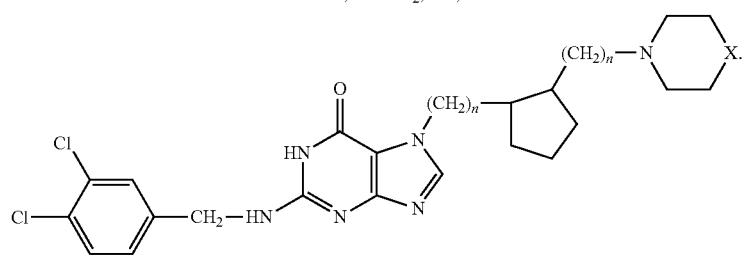

n = 1 or 2; X = CH$_2$, NH, O

Specific compounds of the invention include 7-[2-(N-morpholinyl)ethyl-2-(3,4-dichlorobenzylamino)-6-oxopurine (cpd 362E); 7-[2-(N-morpholinyl)ethyl-2-(3,4-dichlorobenzylamino)-6-oxopurine hydrochloride; 7-[3-(N-morpholinyl)propyl-2-(3,4-dichlorobenzylamino)-6-oxopurine (cpd 363A); 7-[3-(N-morpholinyl)propyl-2-(3,4-dichlorobenzylamino)-6-oxopurine hydrochoride; 7-[4-(N-morpholinyl)butyl]-2-(3,4-dichlorobenzylamino)-6-oxopurine hydrochloride; 7-[5-(N-morpholinyl)pentyl]-2-(3,4-dichlorobenzylamino)-6-oxopurine (cpd 359E); 7-[5-(N-morpholinyl)pentyl]-2-(3,4-dichlorobenzylamino)-6-oxopurine hydrochloride; 7-[2-(N-morpholinyl) ethoxyethyl]-2-(3,4-dichlorobenzylamino)-6-oxopurine; 7-[4-(N-piperidinyl)butyl]-2-(3,4-dichlorobenzylamino)-6-oxopurine; 7-[5-(N-piperidinyl)pentyl]-2-(3,4-dichlorobenzylamino)-6-oxopurine; 7-[2-(N-piperidinyl)ethoxyethyl]-2-(3,4-dichlorobenzylamino)-6-oxopurine; 7-[4-(N-azetidinyl)butyl]-2-(3,4-dichlorobenzylamino)-6-oxopurine; 7-[5-(N-azetidinyl)pentyl]-2-(3,4-dichlorobenzylamino)-6-oxopurine; 7-[2-(N-azetidinyl) ethoxyethyl]-2-(3,4-dichlorobenzylamino)-6-oxopurine; 7-[4-(N-pyrrolidinyl)butyl]-2-(3,4-dichlorobenzylamino)-6-oxopurine; 7-[5-(N-pyrrolidinyl)pentyl]-2-(3,4-dichlorobenzylamino)-6-oxopurine; 7-[2-(N-pyrrolidinyl)ethoxyethyl]-2-(3,4-dichlorobenzylamino)-6-oxopurine; 7-{2-[(N-morpholinyl)methyl]cyclobutylmethyl}-2-(3,4-dichlorobenzylamino)-6-oxopurine; 7-{2-[(N-morpholinyl)methyl]cyclobutylmethyl}-2-(3,4-dichlorobenzylamino)-6-oxopurine hydrochloride; 7-{2-[(N-morpholinyl)methyl]cyclopentylmethyl}-2-(3,4-dichlorobenzylamino)-6-oxopurine hydrochloride; 7-{2-[(N-morpholinyl)methyl]cyclobutylmethyl}-2-(3,4-dichlorobenzylamino)-6-oxopurine; 7-{2-[(N-piperidinyl)methyl]cyclobutylmethyl}-2-(3,4-dichlorobenzylamino)-6-oxopurine; and 7-{2-[(N-piperidinyl)methyl]cyclopentylmethyl}-2-(3,4-dichlorobenzylamino)-6-oxopurine. Additional compounds are 7-[4-(N-morpholinyl)butyl]-2-(3,4-dichlorobenzylamino)-6-oxopurine (cpd 258D) and its hydrochloride salt.

The invention further features a pharmaceutical composition including a compound of the invention and a pharmaceutically acceptable excipient.

The invention also features a method of treating or reducing the likelihood of developing a *C. diff.*-associated disease by administering to an animal in need thereof a therapeutically effective amount of a compound of the invention. Exemplary *C. diff.*-associated diseases include *C. diff.*-associated diarrhea or *C. diff.*-associated colitis. In certain embodiments, the animal is at increased risk for *C. diff.* infection, as described herein.

The invention further features a method of inhibiting growth of *C. diff.* in vitro, the method comprising contacting, in an appropriate culture medium in the absence of oxygen, *C. diff.* with an effective amount of a compound of the invention.

Compounds of the invention may be used as medicaments, e.g., for use in treating or reducing the likelihood of developing a *C. diff.*-associated disease.

By "acyl" is meant —C(O)R, wherein R is alkyl. For example, C$_1$ acyl is acetyl.

By "alkyl" is meant a branched or unbranched saturated acyclic hydrocarbon group, desirably having from 1 to 6 carbon atoms. Examples include methyl; ethyl; n-propyl; isopropyl; n-butyl; iso-butyl; sec-butyl; tert-butyl; pentyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and hexyl. An alkyl group may be unsubstituted or substituted, as described herein.

By "alkoxy" is meant —OR, wherein R is an alkyl group.

By "alkylamino" is meant —NHR, wherein R is an alkyl group.

By "alkylaryl" is meant —RR', wherein R is an aryl group, e.g., of 6 to 12 carbons, and R' is an alkyl group, e.g., of 1 to 8 carbons.

By "alkylsufonyl" is meant —$SO_2R$, wherein R is an alkyl group.

By "alkylthio" is meant —SR, wherein R is an alkyl group.

By "aryl" is meant a monocyclic, bicyclic, or multicyclic carbocyclic ring system having one or more aromatic rings. Each ring preferably includes from 6-12 carbon atoms. Examples include phenyl, naphthyl, 1,2-dihydronaphthyl, 1,2,3,4-tetrahydronaphthyl, fluorenyl, indanyl, and indenyl. An aryl group may be unsubstituted or substituted, as described herein.

By "arylalkyl" is meant —RR', wherein R is an alkyl group, e.g., of 1 to 8 carbons, and R' is an aryl group, e.g., of 6 to 12 carbons.

By "arylamino" is meant —NHR, wherein R is an aryl group.

By "aryloxy" is meant —OR, wherein R is an aryl group.

By "arylthio" is meant —SR, wherein R is an aryl group.

By "cycloalkyl" is meant a monocyclic or bicyclic structure having only carbon atoms in the ring(s), in which each ring desirably has three to six members. Exemplary cycloalkyl groups include cyclopropyl; cyclobutyl; cyclopentyl; and cyclohexyl. A cycloalkyl group may be unsubstituted or substituted, as described herein.

By "disubstituted amino" is meant —NRR', wherein R and R' are independently alkyl, aryl, heteroaryl, and heterocyclyl.

In the context of inhibiting bacterial growth, by "effective amount" of a compound is meant an amount which, when administered in vivo or in vitro, will reduce the cellular growth rate by at least 80%.

By "halo" is meant fluoro, bromo, chloro, or iodo.

By "haloalkyl" is meant an alkyl group substituted with one or more halo groups, e.g., perfluoroalkyl.

By "haloalkoxy" is meant an alkoxy group substituted with one or more halo groups.

By "heteroaryl" is meant a monocyclic, bicyclic, or multicyclic heterocyclic ring system having one or more aromatic rings. Each ring preferably includes 1 to 10, e.g., 2 to 9, carbon atoms and 1 to 4 oxygen, nitrogen, and/or sulfur atoms. Examples include benzimidazolyl, benzofuranyl, benzotriazolyl, furyl, imidazolyl, indolyl, isobezofuranyl, isoquinolinyl, isoxazolyl, oxazolyl, purinyl, pyrazinyl, pyridazinyl, pyridinyl, pyrimidinyl, pyrrolyl, quinolinyl, tetrazolyl, thienyl, triazinyl, and triazolyl. A heteroaryl group may be unsubstituted or substituted, as described herein.

By "heterocyclyl" is meant a monocyclic, bicyclic, or multicyclic heterocyclic ring system not including an aromatic ring. Each ring preferably includes 2 to 9, e.g., 2 to 8, carbon atoms and 1 to 4 oxygen, nitrogen, and/or sulfur atoms. Examples include aziridinyl, azetidinyl, morpholinyl, oxazolidinyl, oxazolinyl, oxecanyl, oxepanyl, oxiranyl, piperazinyl, piperidinyl, pyranyl, pyrrolidinyl, tetrahydrofuranyl, tetrahydropyranyl, tetrahydrothienyl, and tetrahydrothiopyranyl. A heterocyclyl group may be unsubstituted or substituted, as described herein.

By "inhibiting" is meant reducing the cellular growth rate by at least 80%. In certain embodiments, the growth can be inhibited by 90%, 95%, or even 99% or more.

By "oxo" is meant =O.

By "a person susceptible to a *C. diff.* infection" is meant an animal, e.g., a human, that is at increased risk, relative to the general population, of contracting a *C. diff.* infection. Examples of such persons include those that have recently undergone antibiotic treatment for another bacterial infection, the young and the elderly. Such persons can be identified using methods known to one of ordinary skill in the art.

By "pharmaceutically acceptable salts" are meant those derived from pharmaceutically acceptable inorganic and organic bases. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like. Additional salts include nontoxic ammonium, quaternary ammonium, and amine cations, including, but not limited to, ammonium, tetramethylammonium, tetraethylammonium, methylamine, dimethylamine, trimethylamine, triethylamine, ethylamine and the like. Pharmaceutically acceptable cations are those salt-forming ions with a positive charge. References hereinafter to a compound according to the invention include compounds of the general formulae shown, as well as their pharmaceutically acceptable salts.

The term "pharmaceutical composition," as used herein, represents a composition containing a compound described herein, formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

By "quaternary amino" is meant —NRR'R"+, wherein R, R', and R" are independently alkyl, aryl, heteroaryl, and heterocyclyl.

By "substituted" is meant that one or more hydrogen atoms of a group or portion of a group are replaced by substituents, including, but not limited to, $C_{1-6}$ alkoxy (e.g., $C_{1-4}$), $C_{6-12}$ aryloxy, sulfhydryl (—SH), $C_{1-6}$ alkylthio, $C_{6-12}$ arylthio, amino (—NH$_2$), $C_{1-6}$ alkylamino, $C_{6-12}$ arylamino, disubstituted amino, quaternary amino, hydroxyl (—OH), carboxyl (—COOH), halogen, cyano (—CN), azido (—N$_3$), oxo, —C(O)—$C_{1-6}$ alkyl, C(O)—$C_{3-8}$ cycloalkyl, —C(O)—$C_{6-12}$ aryl, —C(O)—$C_{5-12}$ heteroaryl, —C(O)—$C_{2-9}$ heterocyclyl, $C_{1-6}$ alkylsulfonyl, —(SO$_2$)O—$C_{1-6}$ alkyl, —(SO$_2$)—$C_{3-8}$ cycloalkyl, —(SO$_2$)O—$C_{3-8}$ cycloalkyl, —(SO$_2$)—$C_{6-12}$ aryl, —(SO$_2$)O—$C_{6-12}$ aryl, —(SO$_2$)—$C_{5-12}$ heteroaryl, —(SO$_2$)O—$C_{5-12}$ heteroaryl, —(SO$_2$)—$C_{2-9}$ heterocyclyl, and —(SO$_2$)O—$C_{2-9}$ heterocyclyl. In addition, alkyl, aryl, cycloalkyl, heteroaryl, and heterocyclyl groups may be substituted with $C_{6-12}$ aryl, $C_{3-8}$ cycloalkyl, $C_{4-12}$ heteroaryl (e.g., $C_{4-6}$ or $C_{5-12}$ heteroaryl), or $C_{2-12}$ heterocyclyl (e.g., $C_{2-9}$ or $C_{5-12}$ heterocyclyl) groups. Cycloalkyl, heteroaryl, and heterocyclyl groups may also be substituted with an alkyl group. Substituents can in turn be substituted as described for the parent groups, e.g., with, halogen, trifluoromethyl, hydroxyl, or carboxyl.

By "therapeutically effective amount" is meant an amount which, when administered to an animal in need, will alleviate at least some of the symptoms of *C. diff.* infection. In the context of prophylaxis, a "therapeutically effective amount" is an amount which, when administered to a person susceptible to *C. diff.* infection, will help inhibit or reduce the likelihood of such an infection.

The term "reducing the likelihood of developing," as used herein, refers to prophylactic treatment or treatment resulting in a reduction (e.g., at least 5%, 10%, 15%, 20%, 25%, 30%, 35%, 40%, 50%, 60%, 70%, 80%, 90%, or 95%) for a subject or a patient population in the chance or rate of developing a *C. diff.*-associated disease by administering a compound of the invention compared to a subject or patient population not receiving the compound. Preventive treatment can be initiated, for example, prior to ("pre-exposure prophylaxis") or following ("post-exposure prophylaxis") an event that precedes the onset of *C. diff.* infection. Preventive treatment that includes administration of a compound of the invention, or a pharmaceutical composition thereof, can be acute, short-term, or chronic. The doses administered may be varied during the course of preventive treatment. The term also includes prevention of activity in vitro.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The details of one or more embodiments of the invention are set forth in the accompanying description below. Other features, objects, and advantages of the invention will be apparent from the description and from the claims.

DETAILED DESCRIPTION OF THE INVENTION

Figure 1A:
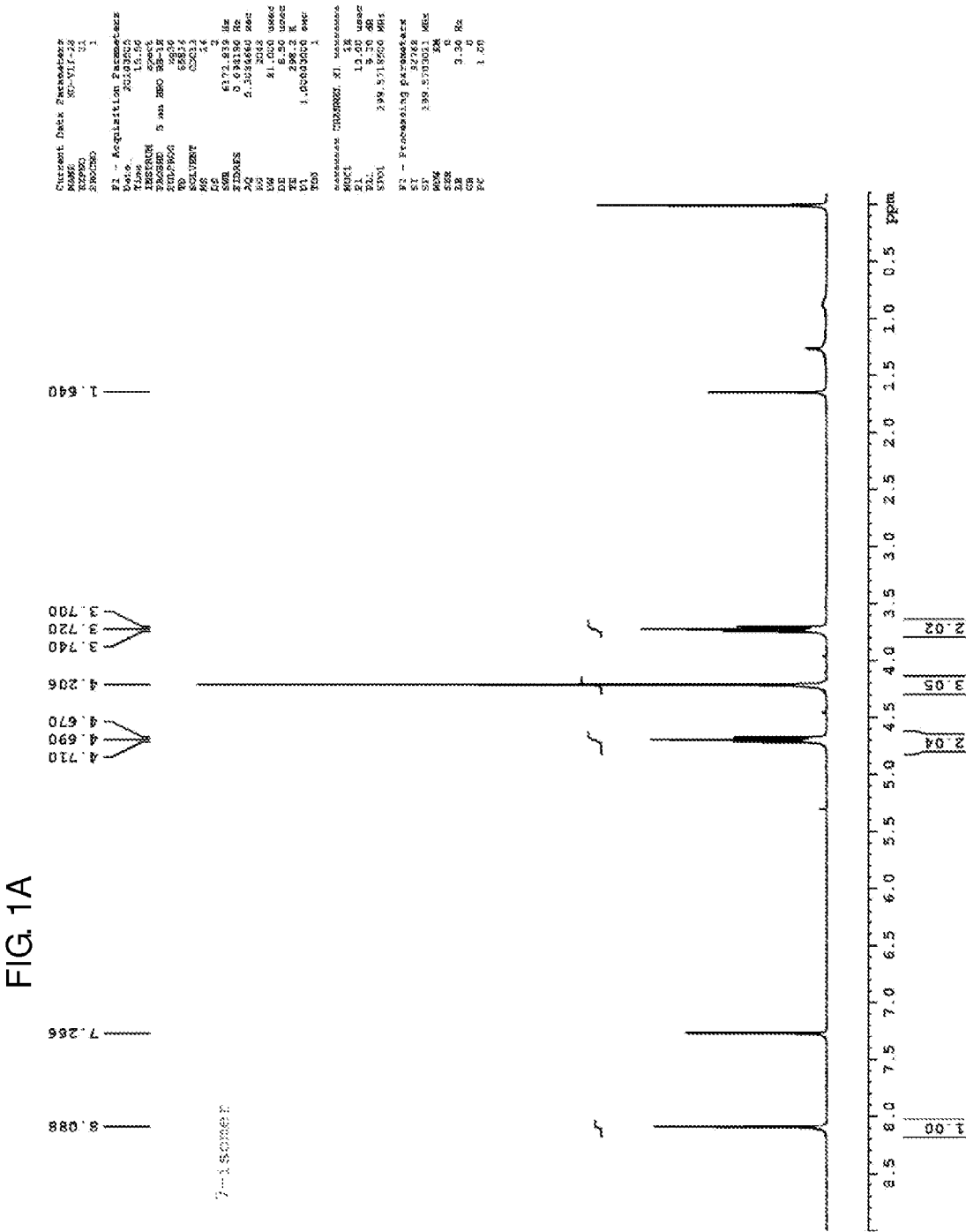
FIG. 1: A) $^1$H-NMR spectrum of 7-(2-bromoethyl)-2-chloro-6-methoxypurine; B) $^1$H-NMR spectrum of 9-(2-bromoethyl)-2-chloro-6-methoxypurine; and C) $^{13}$C-NMR spectrum of 7-(2-bromoethyl)-2-chloro-6-methoxypurine.

The invention features methods and compositions for treating infections caused by or associated with *C. diff.* Compound of the invention have the formula:

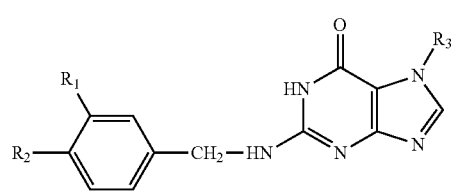

wherein $R^1$ and $R^2$ are, independently, H, halo, $C_{1-6}$ haloalkyl, or $C_{1-6}$ haloalkoxy;

wherein $R^3$ is $(CH_2)_m$-$\{(A)_o$-$(CH_2)_p\}_q$—B;

in which A is $CH_2$, CH=CH, C≡C, CO, O, S, NR$^6$, CHR$^7$, OC(O), (O)CO, CONR$^{10}$, NR$^{11}$CO, SO$_2$NH, NHSO$_2$, or $C_{3-8}$ cycloalkyl, wherein each R$^6$, R$^{10}$, and R$^{11}$ is, independently, H or $C_{1-6}$ alkyl; R$^7$ is OH or $C_{1-6}$ alkyl; and each of R$^8$ and R$^9$ is, independently, H, halo, or $C_{1-6}$ alkyl;

in which B is H, halo, substituted or unsubstituted $C_{1-10}$ alkyl, substituted or unsubstituted $C_{3-8}$ cycloalkyl, substituted or unsubstituted $C_{2-8}$ heterocyclyl or $C_{1-10}$ heteroaryl, NH$_2$, CN, OR$^{12}$, SR$^{13}$, COR$^{14}$, OCOR$^{15}$, NR$^{16}$COR$^{17}$, NR$^{18}$R$^{19}$, NR$^{20}$CONHR$^{21}$, CN, CH(CO$_2$R$^{22}$)$_2$, CO$_2$R$^{23}$, NHSO$_2$R$^{24}$, CONR$^{25}$R$^{26}$, or CH$_2$COR$^{27}$, in which each of R$^{12}$-R$^{27}$ is, independently, H, substituted or unsubstituted $C_{1-6}$ alkyl, substituted or unsubstituted $C_{3-8}$ cycloalkyl, substituted or unsubstituted $C_{6-12}$ aryl, substituted or unsubstituted $C_{7-20}$ arylalkyl, substituted or unsubstituted $C_{7-20}$ alkylaryl, substituted or unsubstituted $C_{2-8}$ heterocyclyl or $C_{4-10}$ heteroaryl, substituted or unsubstituted $C_{1-3}$ acyl, or substituted or unsubstituted $C_{1-6}$ alkylsulfonyl;

m is 1-5, o is 0-4, p is 0-4, and q is 0-4;

or an optical isomer thereof.

It will be understood that the substituents selected for $R_{1-3}$ will result in a stable compound in which valency requirements are fulfilled. For example, compounds with O—O, O—S, O-halo, S-halo, or N-halo bonds are excluded from formula I.

In one series of embodiments, $R^1$ and $R^2$ are chloro, and $R^3$ is 2-(N-morpholinyl)ethyl, 3-(N-morpholinyl)propyl, 4-(N-morpholinyl)butyl, 5-(N-morpholinyl)pentyl, 2-[(N-morpholinyl)ethoxy]ethyl, 2-[(N-morpholinyl)-methyl]cyclobutylmethyl, or 2-[(N-morpholinyl)methyl]cyclopentylmethyl. In some compounds, $R^1$ and $R^2$ are selected, independently, from the group consisting of Cl, Br, I, $CF_3$, $OCF_3$, $CF_2CF_3$, and $CH_2CF_3$. In yet other compounds, $R^3$ is selected from the group consisting of ω-(N-aziridinyl)alkyl, ω-(N-pyrrolidinyl)alkyl ω-(N-piperidinyl)alkyl, and ω-(N-piperazinyl)alkyl.

Compounds that have selective antibacterial activity against *C. diff.* species include certain 7-substituted-2-(benzylamino)-6-oxopurines of the general structures:

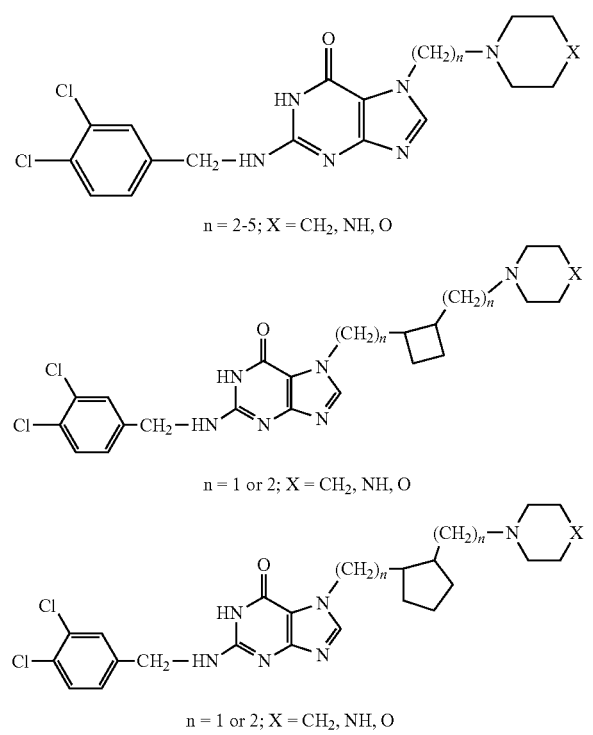

Preferred compounds include:
7-[2-(N-morpholinyl)ethyl-2-(3,4-dichlorobenzylamino)-6-oxopurine (cpd 362E);
7-[2-(N-morpholinyl)ethyl-2-(3,4-dichlorobenzylamino)-6-oxopurine hydrochloride;
7-[3-(N-morpholinyl)propyl-2-(3,4-dichlorobenzylamino)-6-oxopurine (cpd 363A);
7-[3-(N-morpholinyl)propyl-2-(3,4-dichlorobenzylamino)-6-oxopurine hydrochoride;
7-[4-(N-morpholinyl)butyl]-2-(3,4-dichlorobenzylamino)-6-oxopurine (cpd 258D);
7-[4-(N-morpholinyl)butyl]-2-(3,4-dichlorobenzylamino)-6-oxopurine hydrochloride;
7-[5-(N-morpholinyl)pentyl]-2-(3,4-dichlorobenzylamino)-6-oxopurine (cpd 359E);
7-[5-(N-morpholinyl)pentyl]-2-(3,4-dichlorobenzylamino)-6-oxopurine hydrochloride;
7-[2-(N-morpholinyl)ethoxyethyl]-2-(3,4-dichlorobenzylamino)-6-oxopurine;
7-[4-(N-piperidinyl)butyl]-2-(3,4-dichlorobenzylamino)-6-oxopurine;
7-[5-(N-piperidinyl)pentyl]-2-(3,4-dichlorobenzylamino)-6-oxopurine;
7-[2-(N-piperidinyl)ethoxyethyl]-2-(3,4-dichlorobenzylamino)-6-oxopurine;
7-[4-(N-azetidinyl)butyl]-2-(3,4-dichlorobenzylamino)-6-oxopurine;
7-[5-(N-azetidinyl)pentyl]-2-(3,4-dichlorobenzylamino)-6-oxopurine;
7-[2-(N-azetidinyl)ethoxyethyl]-2-(3,4-dichlorobenzylamino)-6-oxopurine;
7-[4-(N-pyrrolidinyl)butyl]-2-(3,4-dichlorobenzylamino)-6-oxopurine;
7-[5-(N-pyrrolidinyl)pentyl]-2-(3,4-dichlorobenzylamino)-6-oxopurine;
7-[2-(N-pyrrolidinyl)ethoxyethyl]-2-(3,4-dichlorobenzylamino)-6-oxopurine;
7-{2-[(N-morpholinyl)methyl]cyclobutylmethyl}-2-(3,4-dichlorobenzylamino)-6-oxopurine;
7-{2-[(N-morpholinyl)methyl]cyclobutylmethyl}-2-(3,4-dichlorobenzylamino)-6-oxopurine hydrochloride;
7-{2-[(N-morpholinyl)methyl]cyclopentylmethyl}-2-(3,4-dichlorobenzylamino)-6-oxopurine hydrochloride;
7-{2-[(N-morpholinyl)methyl]cyclobutylmethyl}-2-(3,4-dichlorobenzylamino)-6-oxopurine;
7-{2-[(N-piperidinyl)methyl]cyclobutylmethyl}-2-(3,4-dichlorobenzylamino)-6-oxopurine; and
7-{2-[(N-piperidinyl)methyl]cyclopentylmethyl}-2-(3,4-dichlorobenzylamino)-6-oxopurine.

The low oral bioavailability of these compounds in mammals endows this class of agents with the characteristics advantageous for alleviating an intestinal infection, e.g., with *C. diff.*

Mechanism of Action

Without wishing to be bound by theory, the compounds target an essential enzyme in DNA replication that has not previously been a target for any marketed antibiotic; thus, development of drug resistance will be minimized. The compounds can be used to circumvent the natural and acquired resistance of pathogenic *C. diff.* to conventional antimicrobials, for example vancomycin and metronidazole.

Genome sequence analysis has indicated that Gram-positive eubacteria of the so-called low G:C class, i.e., those with genomes containing a proportion of guanine+cytosine of less than 0.5, contain two types of DNA polymerase III (pol III): pol IIIC, encoded by a polC gene, and pol IIIE, encoded by one or more dnaE genes, (See, Wright, G. and Brown, N. Current Opinion in Anti-Infective Investigational Drugs 1:45-48 (1999) and Braithewaite, D. and Ito, J. Nucl. Acids Res. 21:787-802 (1993)). The compounds described herein were designed to inhibit either or both of the pol IIIC and pol IIIE enzymes.

Gram-positive pol IIIC and Gram-positive pol IIIE are enzymes that are both required for the replicative synthesis of DNA that accompanies the duplication of the Gram-positive bacterial chromosome. Gram-negative pol IIIE is the enzyme that is required for the replicative synthesis of DNA that accompanies the duplication of the Gram-negative bacterial chromosome. The compounds described herein mimic purine deoxyribonucleoside-5-triphosphates and physically inhibit the DNA polymerases. The mechanism of action of related N3-substituted pyrimidines is further described in U.S. Pat. No. 5,516,905. Because certain of the compounds described herein inhibit the DNA polymerases from both aerobic and anaerobic Gram-positive bacteria, they are in principle useful for inhibiting the growth of these bacteria. However, the results shown herein indicate selectivity for inhibiting the growth of *C. diff.* strains, sparing other Gram-positive anaerobic bacteria.

Methods of Synthesis

The compounds may be synthesized by methods that are generally described in U.S. Pat. No. 6,926,763. In particular, U.S. Pat. No. 6,926,763 describes the preparation of the intermediates, 7-(4-bromobutyl)DCBG and 7-(5-iodopentyl) DCBG, used to prepare the compounds of the invention.

An improved method of synthesis of some compounds utilizes the following scheme, showing as an example the synthesis of compound 363A, starting with the well known 2-chloro-6-methoxypurine.

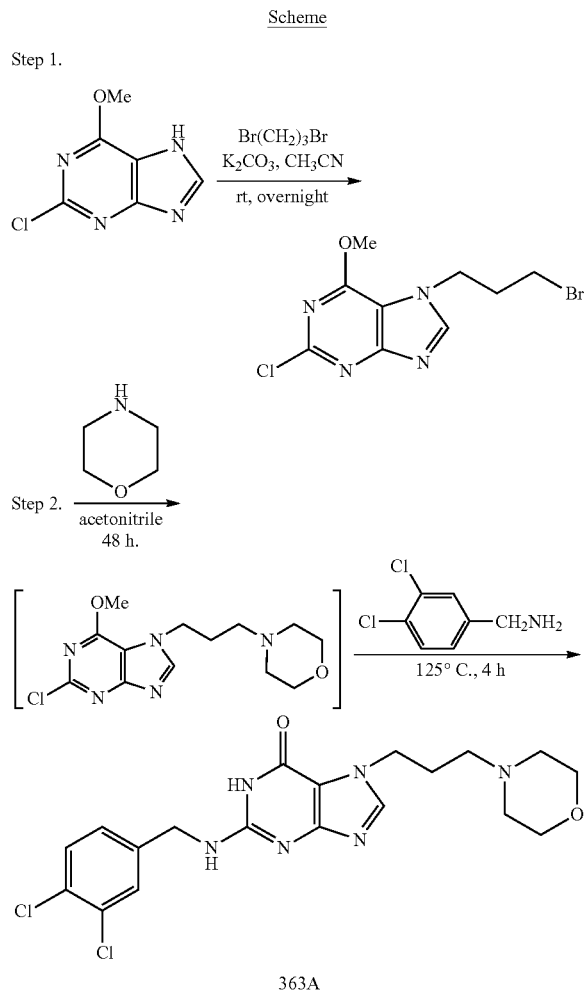

Uses of the Compounds

Compounds of the invention can be used to inhibit growth of *C. diff.* and to treating or reducing the likelihood of developing a *C. diff.*-associated disease. The methods for inhibiting the growth of *C. diff.* involve administering an effective amount of a compound of the invention. The degree of inhibition can be ascertained by an in vitro growth assay, e.g., by a standard liquid culture technique. Compounds showing inhibition of colony formation at suitable MICs (minimal inhibitory concentrations), e.g. <10 µg/ml, are useful for as therapeutic agents. The method for treating or reducing the likelihood of developing a *C. diff.*-associated infection involves administering a therapeutically effective amount of a compound of the invention, preferably by the oral route.

The compounds described herein are useful for the treatment of *C. diff.*-associated diseases, such as *C. diff.*-associated diarrhea (CDAD) or colitis, including disease caused by highly virulent and antibiotic-resistant strains of *C. diff.* The compounds are useful for the treatment of such infections in humans and other animals, such as pigs, cows, horses, goats, chickens, turkeys, sheep, rats, mice, and rabbits.

In one embodiment, a compound or composition of the invention is administered to a subject that has been diagnosed with a *C. diff.*-associated infection. The compounds can be administered both prophylactically and after infection has occurred. Prophylaxis can be most appropriate for patients at risk for infection or for recurrence of an infection.

The compounds can be administered a person susceptible to a *C. diff.* infection. Susceptibility to *C. diff.* infection may occur as a result of antibiotic exposure, gastrointestinal surgery/manipulation, prolonged length of stay in a healthcare setting (e.g., greater than 1 week), serious underlying illness, immune-compromising conditions, aging, use of proton pump inhibitors, malignancy, chronic obstructive pulmonary disease, immunosuppressive or anti-peristaltic medications, inflammatory bowel disease, renal failure, hypoalbuminemia, and organ transplant. Peripartum women are also at increased risk of *C. diff.*-associated infection. Antibiotics that may increase susceptibility to *C. diff.*-associated infection include clindamycin, penicillins, cephalosporins, and fluoroquinolones.

Compounds of the invention may also be used in combination with other agents for treating or reducing the likelihood of developing *C. diff.*-associated infections including vancomycin, metronidazole, and nitazoxanide.

This list of relevant conditions for application of the methods of the invention is not intended to be limiting, and any appropriate infection responsive to the compounds can be treated using the methods and/or compounds described herein.

Pharmaceutical Compositions

The compounds of the invention may be formulated into pharmaceutical compositions for administration to human or animal subjects in a biologically compatible form suitable for administration in vivo or in vitro. Accordingly, the present invention provides a pharmaceutical composition including a compound of the invention in admixture with an excipient.

In accordance with the methods of the invention, the described compounds or salts thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time. For human or animal use, the formulations of this invention can be administered by the oral, buccal, rectal and vaginal routes, or by topical administration.

The formulations of this invention may also be administered by the use of surgical implants which release the compounds of the invention, either as a bolus or slowly over a pre-selected period of time.

Without limitation, for oral administration, formulations can be, for example, in the form of tablets, capsules, liquid solutions and suspensions (wherein such solutions and suspensions are particularly for formulations intended for pediatric use).

A compound of the invention may also be administered parenterally. Solutions of a water-soluble compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003—20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that it is easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable excipients, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, the compounds of the invention can be provided in an aqueous physiological buffer solution containing about 0.1 to 10% w/v compound or in a solid dosage form such as a tablet or capsule. General dose ranges are from about 0.01 mg/kg to about 1 g/kg of body weight per day.

Water Solubility

The compounds described herein generally have low water solubility; however, some of the compounds can form salts, such as with inorganic or organic acids, thus greatly increasing their water solubilities. The improved water solubilities are a distinct advantage in formulation and in dosing of animals for testing, and for ultimate therapeutic use in humans. Preferred pharmaceutically acceptable salts are hydrochloride salts. Other salts are described herein.

EXAMPLES

The following specific examples are to be construed as merely illustrative, and not limitative of the remainder of the disclosure in any way.

Example 1

Synthesis of Representative Compounds

Compound 362E.

Figure 1B:
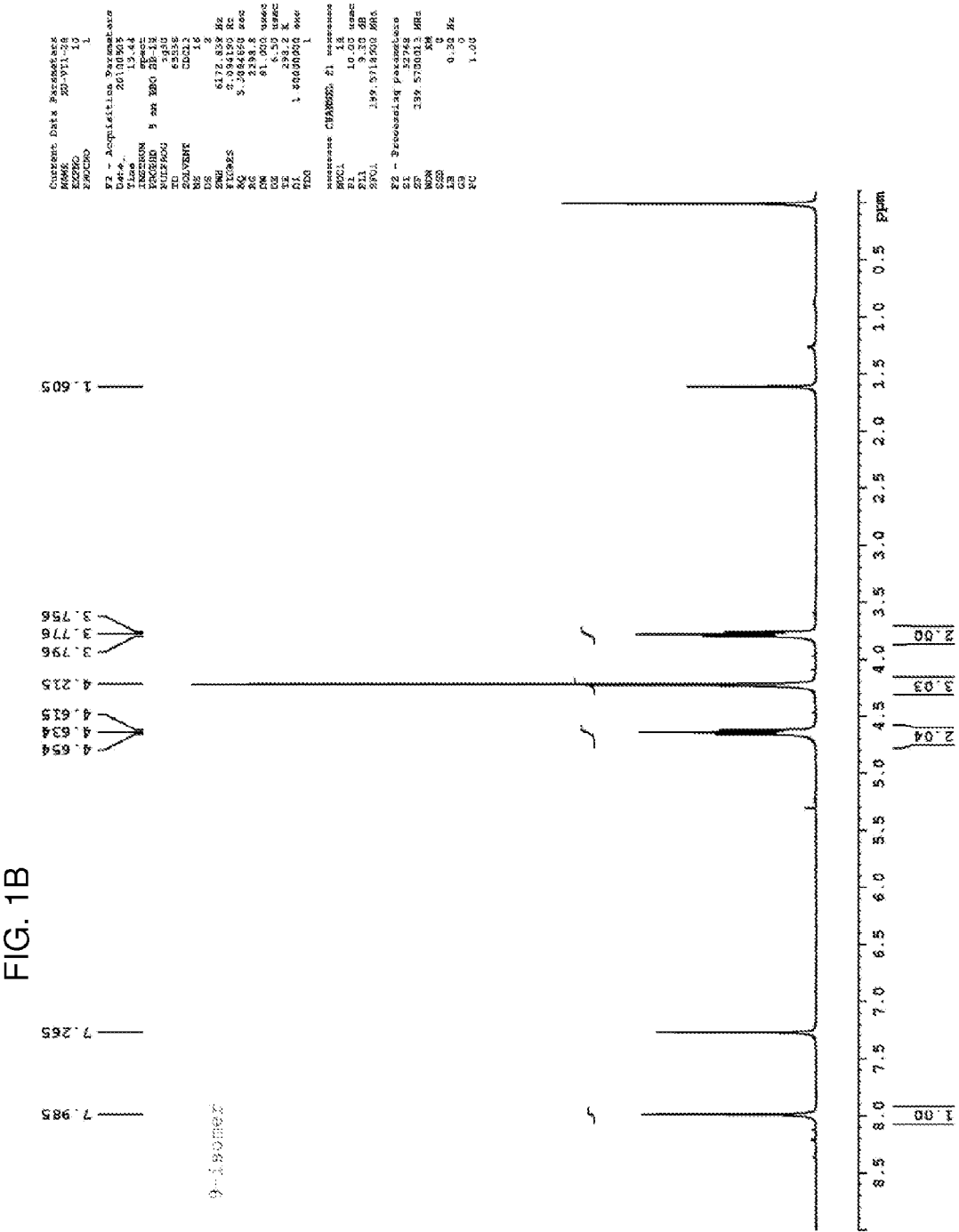
Figure 1C:
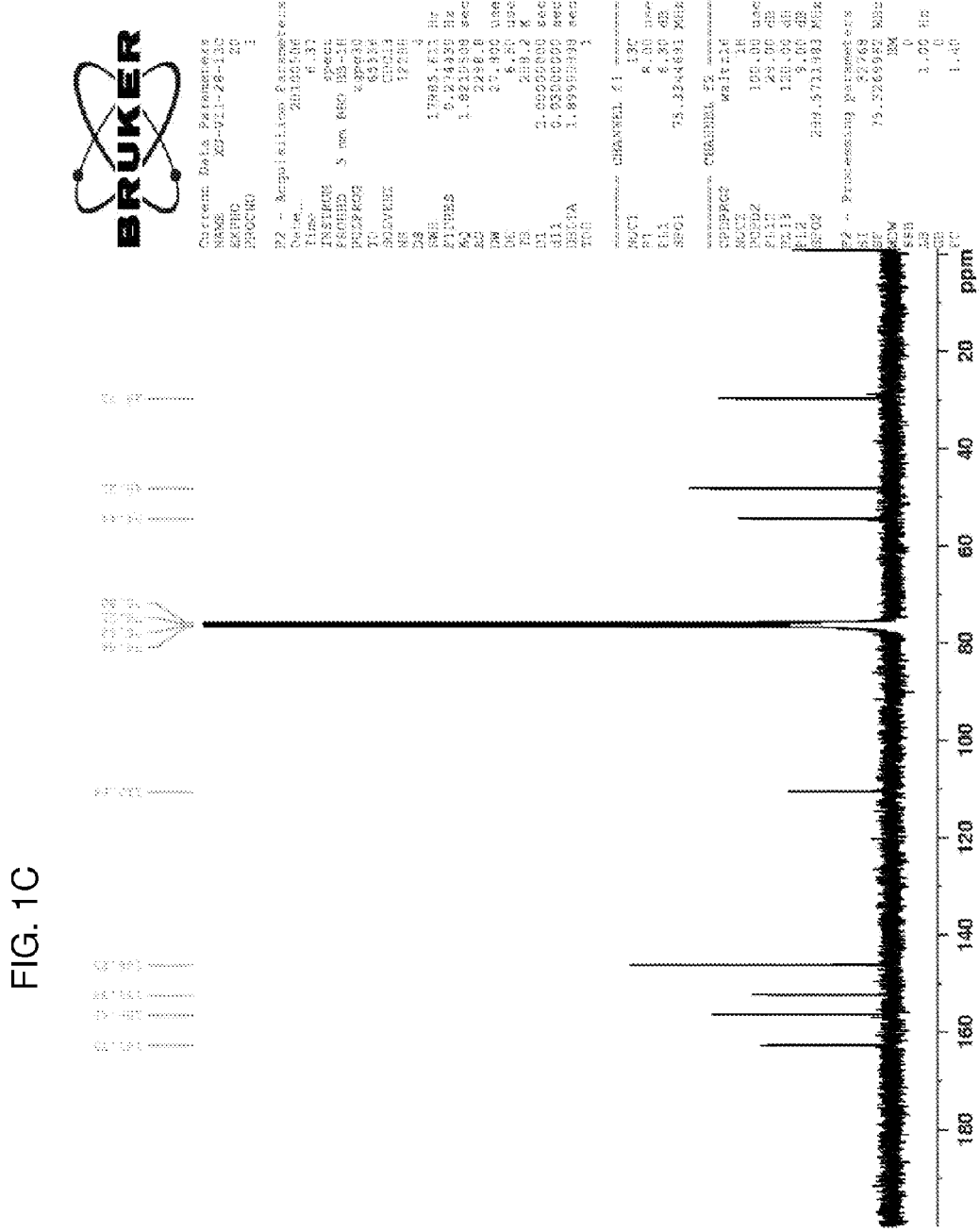

Step 1. Potassium carbonate (1.38 g, 10 mmol) was added to a solution of 2-chloro-6-methoxypurine (830 mg, 4.5 mmol) in acetonitrile (40 mL). The suspension was stirred at room temperature for 10 minutes, after which 1,2-dibromo-ethane (5.64 g, 30 mmol) and tetrabutylammonium iodide (37 mg, 0.1 mmol) were added. The mixture was stirred in an oil bath at 45° C. for 48 hours. The mixture was removed from the oil bath, and the solvent was removed on a rotary evaporator at 45° C. The residue was applied to silica gel column, and washing with 0.7% methanol:methylene chloride afforded first the 7-isomer (289 mg, 22%) and the 9-isomer (380 mg, 29%). The $^1$H NMR spectra of both are shown in FIGS. 1A-1B, and the $^{13}$C NMR spectrum of the 7-isomer is shown in FIG. 1C.

Figure 2:
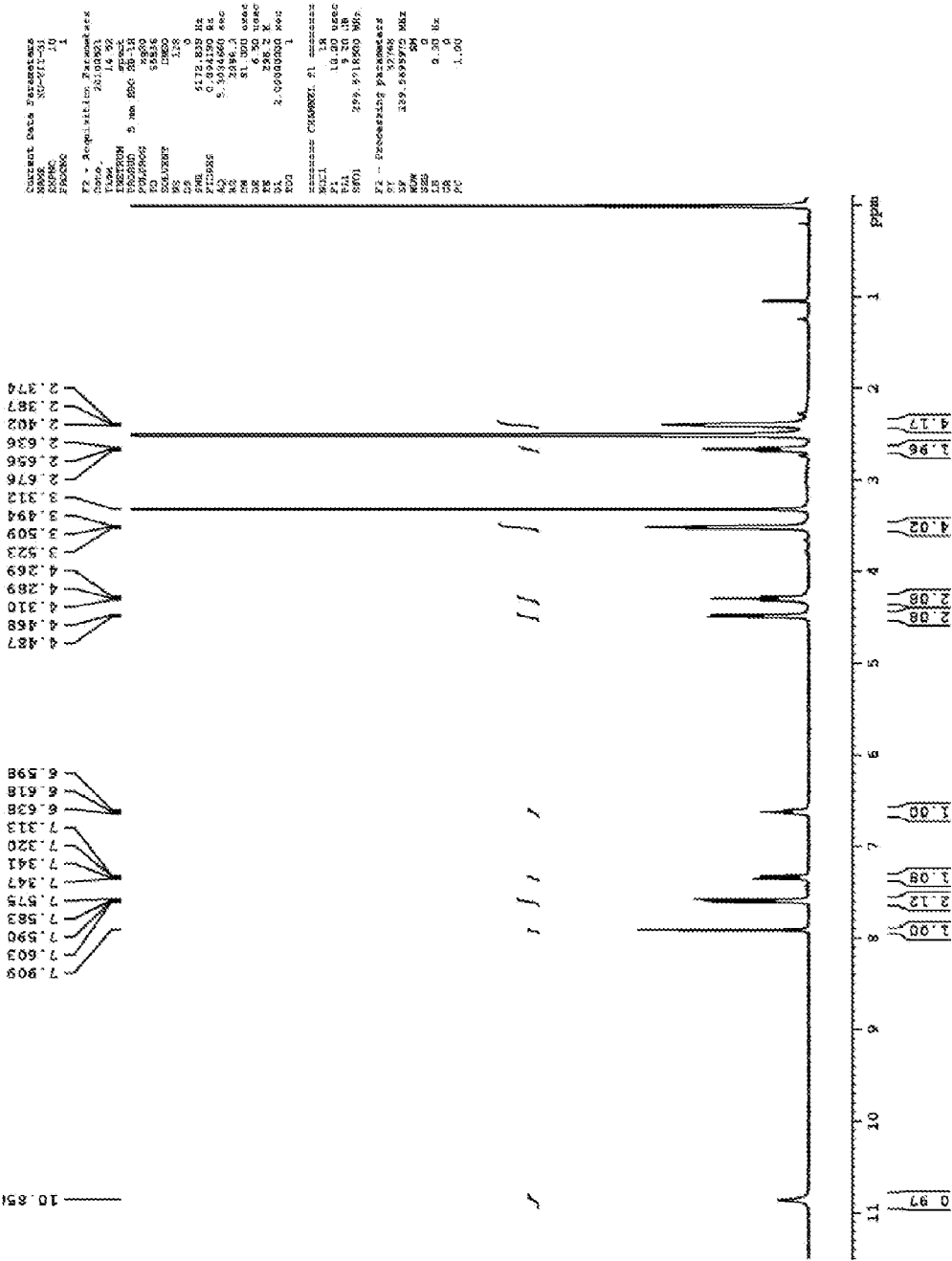
FIG. 2: $^1$H-NMR spectrum of compound 362E.

Step 2. Morpholine (87 mg, 1 mmol) was added to a suspension of 7-(2-bromoethyl)-2-chloro-6-methoxypurine (80 mg, 0.275 mmol) in acetonitrile (6 mL), and the mixture was stirred at 50° C. overnight. The reaction mixture was concentrated <50° C. on a rotary evaporator under high vacuum (0.1 mmHg), and the residue was used directly in the next reaction. 3,4-Dichlorobenzylamine (352 mg, 2 mmol) was added to the above residue, and the mixture was stirred at 125° C. for 4 hours. The cooled mixture was applied to a silica gel column, and the column was washed with 6% methanol:chloroform. The product was crystallized from 2-propanol to obtain 28 mg pure and 40 mg of ca. 90% pure 362E (ca. 56% overall). The $^1$H NMR spectrum is shown in FIG. 2.

Compound 363A

Figure 3A:
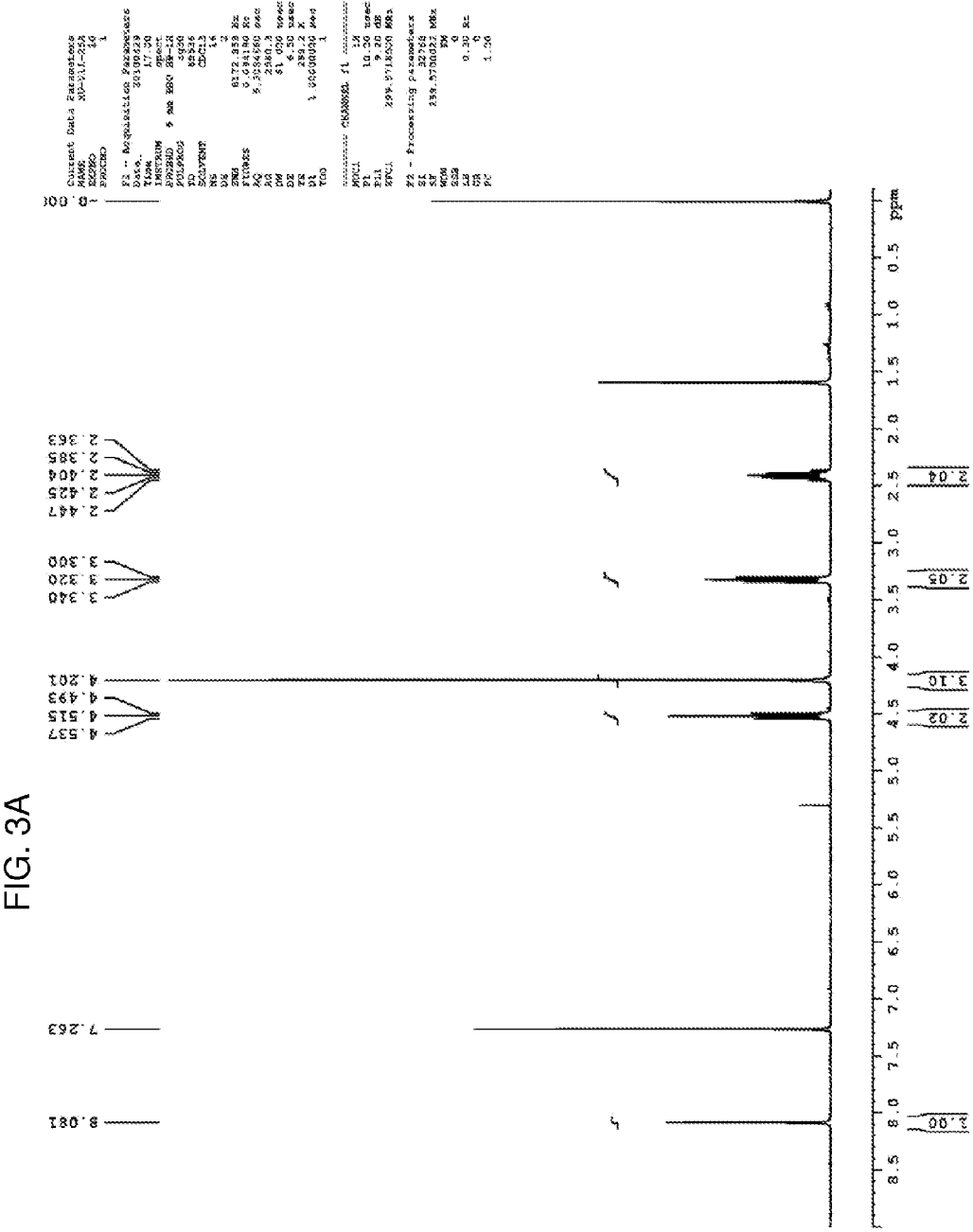
FIG. 3: A) $^1$H-NMR spectrum of 7-(3-bromopropyl)-2-chloro-6-methoxypurine; B) $^1$H-NMR spectrum of 9-(3-bromopropyl)-2-chloro-6-methoxypurine; and C) $^{13}$C-NMR spectrum of 7-(3-bromopropyl)-2-chloro-6-methoxypurine.
Figure 3B:
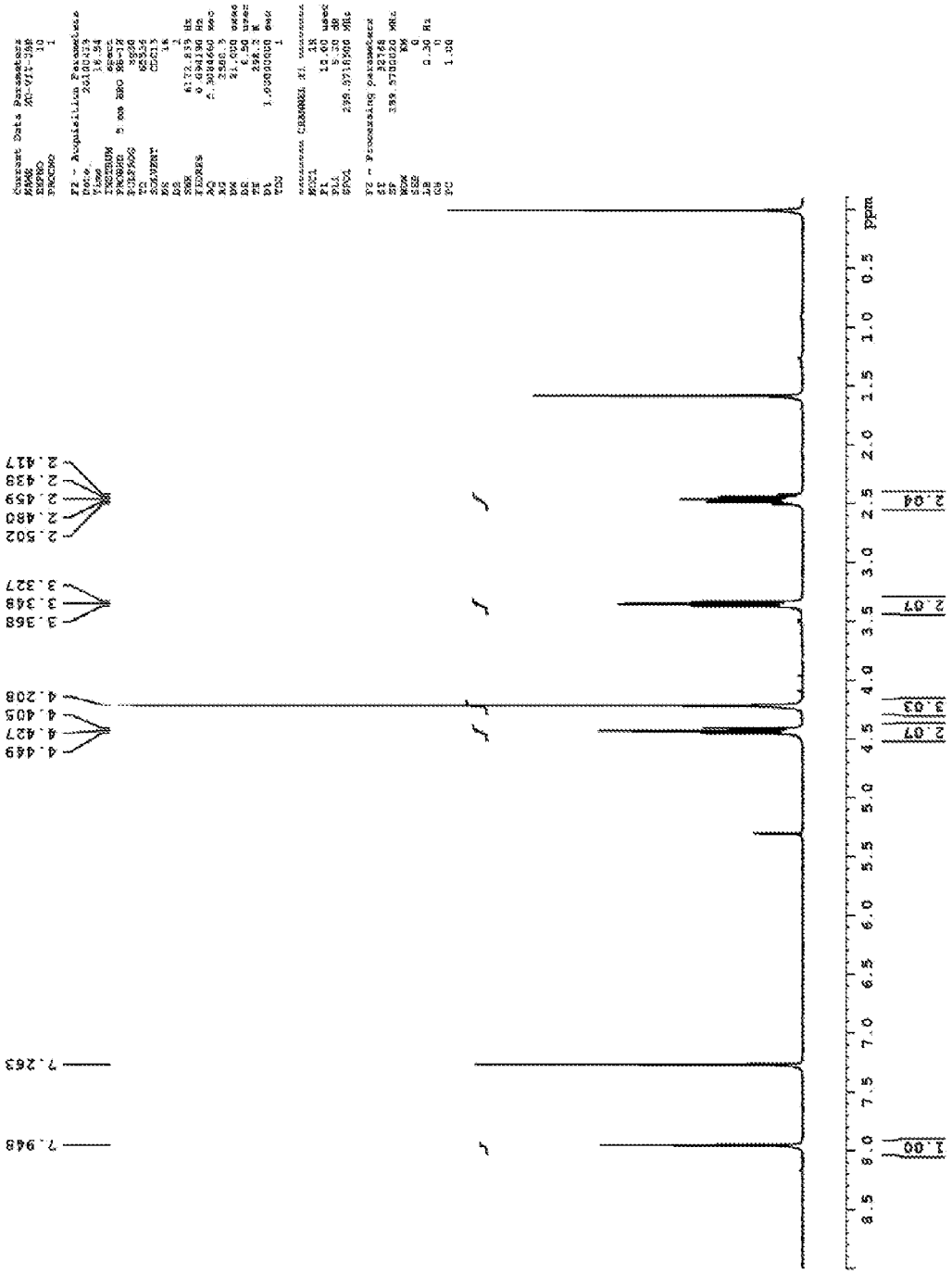
Figure 3C:
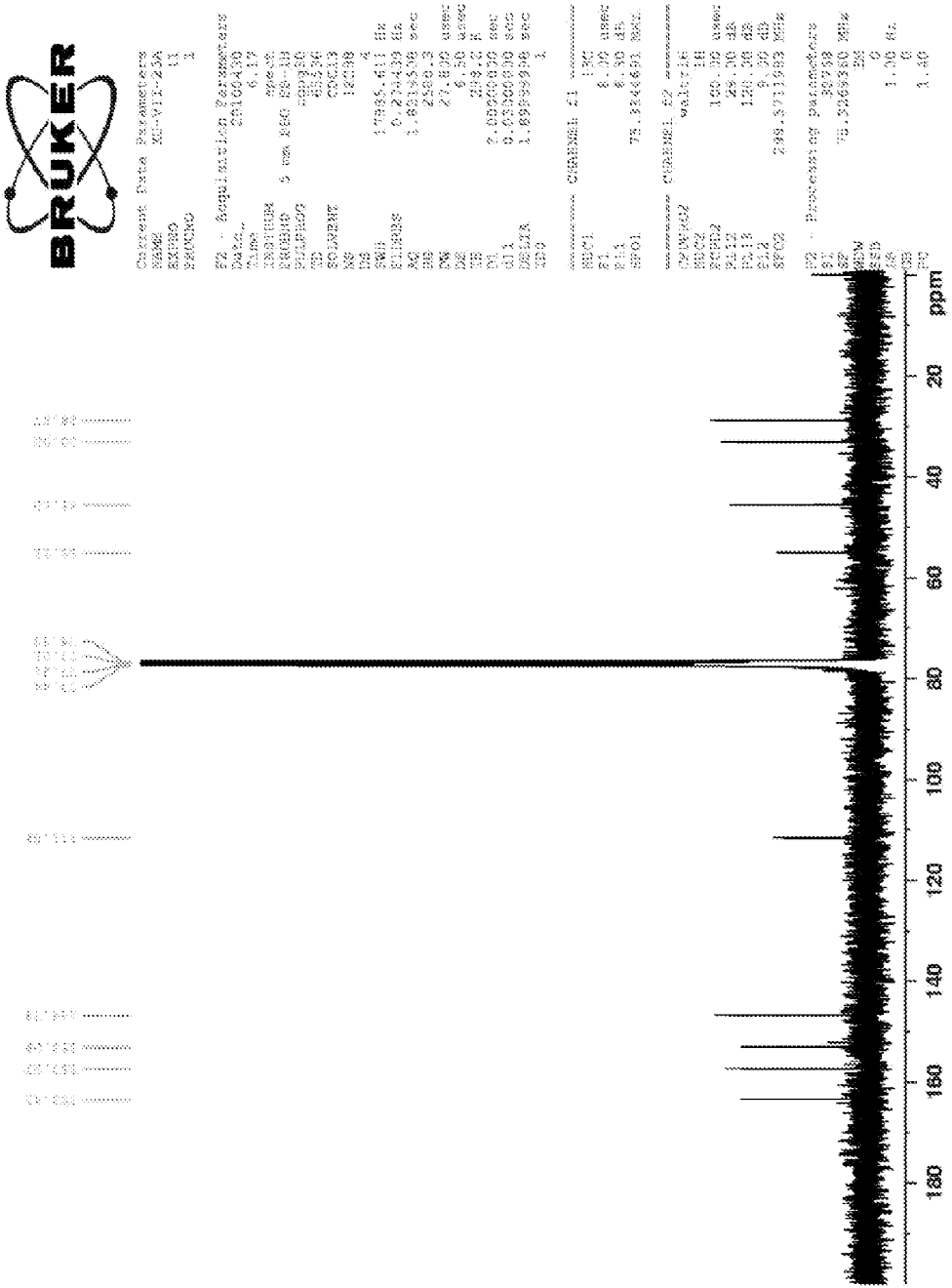

Step 1. Potassium carbonate (552 mg, 4 mmol) was added to a suspension of 2-chloro-6-methoxypurine (553.5 mg, 3 mmol) in acetonitrile (15 mL), and the suspension was stirred for 5 minutes. 1,3-Dibromopropane (4.04 g, 20 mmol) was added, and the suspension was stirred at room temperature for 36 hours until starting material almost disappeared (TLC). Solvent was removed on a rotary evaporator, and the residue [isomer ratio of 9:7 was about 1.7:1 by $^1$H NMR] was applied to a silica gel column. Washing with 0.7% methanol:methylene chloride gave first the 7-isomer (250 mg, 27%) and the 9-isomer (420 mg, 46%). The $^1$H NMR spectra of both are shown in FIGS. 3A-3B. The $^{13}$C NMR spectrum of the 7-isomer is shown in FIG. 3C.

Figure 4:
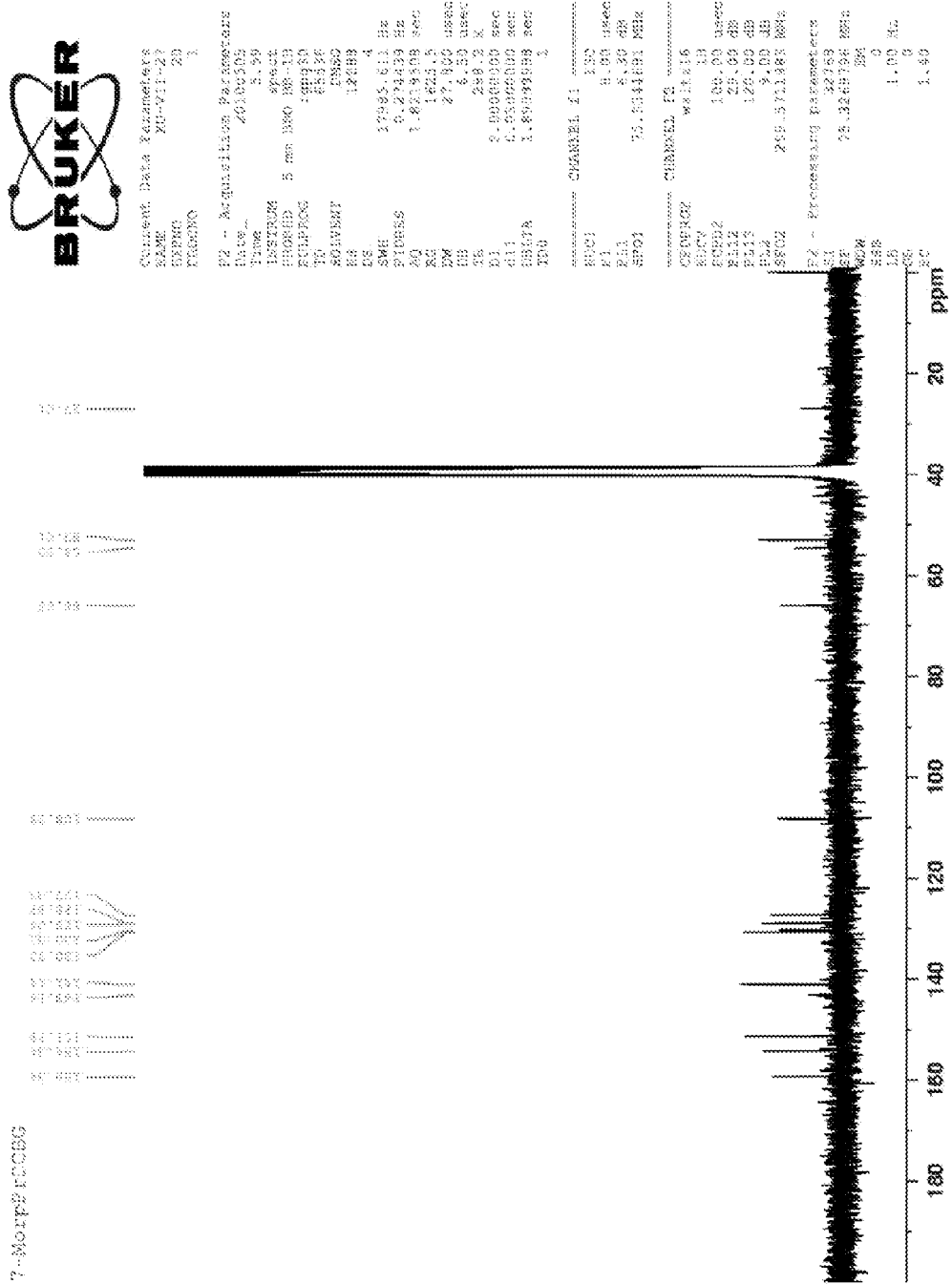
FIG. 4: $^{13}$C-NMR spectrum of compound 363A.

Step 2. Morpholine (0.2 mL) was added to a solution of 7-(3-bromopropyl)-2-chloro-6-methoxypurine (90 mg, 0.295 mmol) in acetonitrile (6 mL) at room temperature. The solution was stirred for 48 hours and followed by TLC to show starting material disappeared. Solvent was removed on a rotary evaporator at room temperature, and the residue was partitioned between methylene chloride (60 mL) and water (30 mL). The aqueous layer was separated and extracted with methylene chloride (2×30 mL). The combined organic extracts were washed with water (1×30 mL) and brine (1×30 mL) and dried over MgSO$_4$. After filtration, the solution was evaporated on a rotary evaporator at room temperature to give 90 mg of intermediate 7-(3-N-morpholinyl)propyl-2-chloro-6-methoxypurine. 3,4-Dichlorobenzylamine (264 mg, 1.5 mmol) was added to the intermediate in a 25 mL conical flask, and the mixture was heated at 125° C. for 4 hours with stirring under argon. The mixture was removed from the oil bath and allowed to come to room temperature in air. Diethyl ether (10 mL) was added, and the mixture was stirred for 5 minutes and stood for 1 hour. The ether layer was decanted, and this procedure was repeated twice. Methanol (6 ml) was added to the residue, and the suspension was stirred for 5 minutes. After standing for 0.5 hour, the precipitate was collected by vacuum filtration and dried in the funnel with suction to afford 50 mg (39% overall) of 363A as a white solid. The $^{13}$C NMR spectrum is shown in FIG. 4.

Compound 359E

Figure 5:
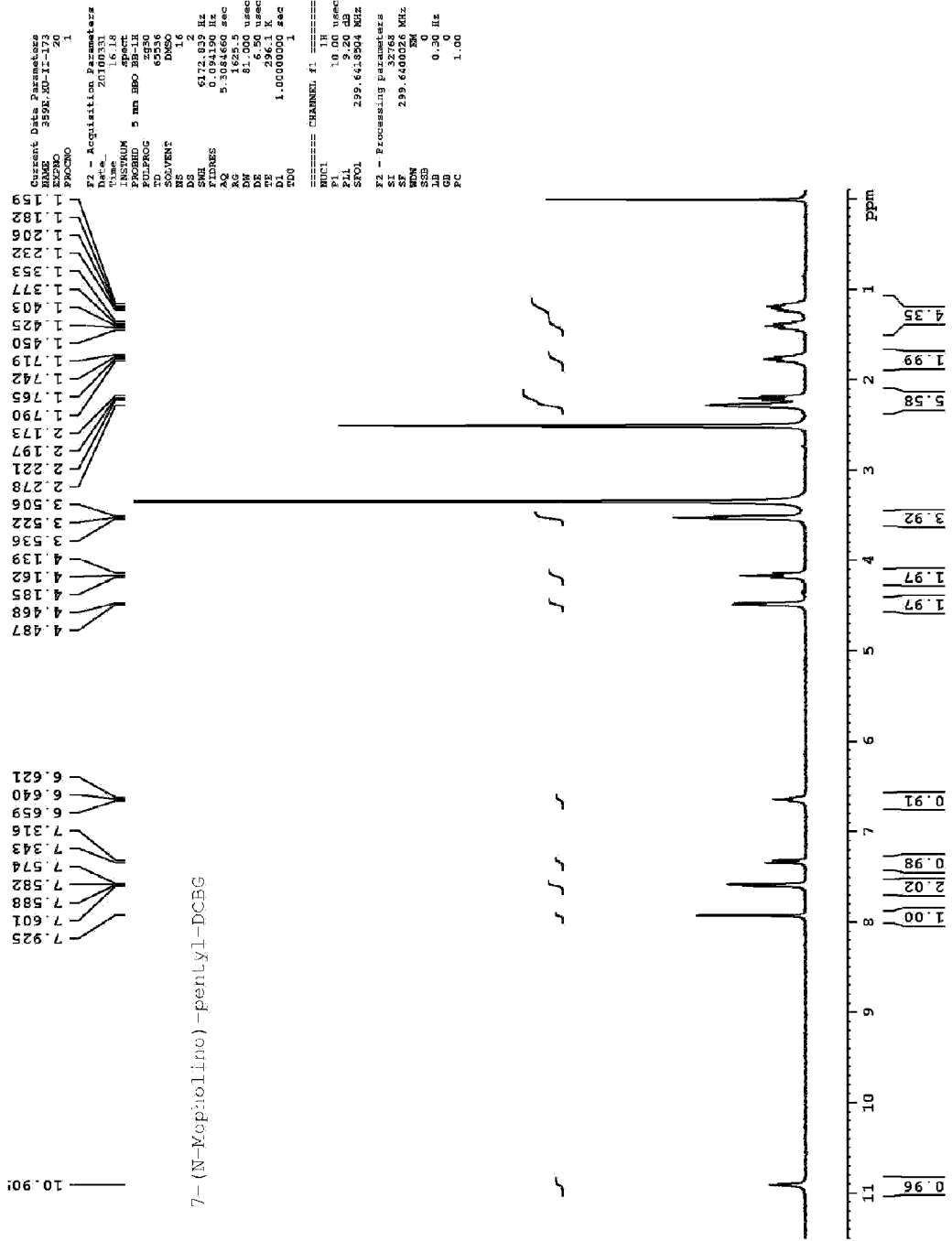
FIG. 5: $^1$H-NMR spectrum of compound 359E.

Step 1. 7-(5-iodopentyl)DCBG (2.5 g, 4.94 mmol) and morpholine (2 mL, 2 g, 21.8 mmol) were refluxed in 60 mL of acetonitrile for 12 hours. The reaction stood at room temperature for 2 hours, and the white precipitate was filtered with suction. The solid was washed with acetonitrile (3×15 mL) followed by water (3×15 mL). The solid was dried at room temperature overnight to give 2.19 g (95%) of white powder. The $^1$H NMR spectrum is shown in FIG. 5.

Example 2

Inhibition of Anaerobic Bacterial Growth by 7-substituted-2-benzylamino-6-oxopurines Each compound was assayed against a panel of anaerobic bacteria in culture, consisting of Gram-positive organisms, such as Lactobacilli, Bifidobacteria, *Clostridium* spp., and Gram-negative bacteria, such as *Bacillus fragilis* spp., according to guidelines of the Clinical and Laboratory Standards Institute (CLSI document M11-A7, CLSI, Wayne, Pa., 2007). A stock solution of test compound in DMSO was diluted with drug-free medium and used to make a series of Petri plates or tubes in a series of two-fold serial dilutions, from about 32 to 0.015 µg/mL. One tenth mL of diluted bacteria containing 500-1000 colony-forming units (CFU) was plated and spread, and the plates incubated at 37° C. for 24-48 hours. MIC (minimum inhibitory concentration) is equivalent to the lowest concentration in µg/ml at which growth, i.e., colony formation, is not observed. Typical results are shown in Tables 1-4.

The medium employed for the agar dilution MIC assay of anaerobic bacteria was *Brucella* Agar supplemented with hemin, Vitamin K$_1$, and 5% lysed sheep blood. Bacteria were assayed using a reference agar dilution method. Drug dilutions and drug-supplemented agar plates were prepared manually. The test organisms were maintained frozen at −80° C. The isolates were sub-cultured on Supplemented *Brucella* Agar (SBA) plates in a Bactron II anaerobic chamber and incubated for 48 hours at 35-36° C. in the Bactron II anaerobe chamber. Following inoculation, the drug-supplemented plates were incubated at 35° C. for 48 hours in the anaerobic environment (5% hydrogen, 5% carbon dioxide, 90% nitrogen) of the Bactron II. The MIC in µg/ml was read per Clinical and Laboratory Standards Institute guidelines.

The compounds whose structures are shown below were tested for inhibiting the growth of Gram-positive anaerobic bacteria, and, for comparison, comparator antibiotics (Table 1). The results show that a compound of formula I, i.e., 332E, was most potent and selective as an anti *C. diff.* compound.

TABLE 1

MICs (µg/ml) of compounds and antibiotics against anaerobes.

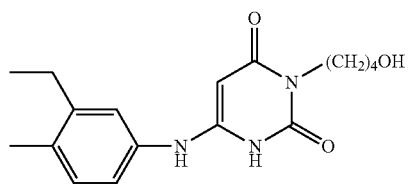

179E

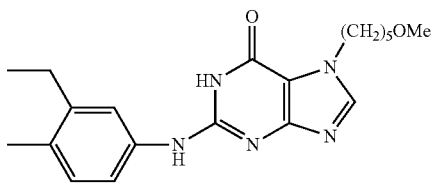

315C

TABLE 1-continued

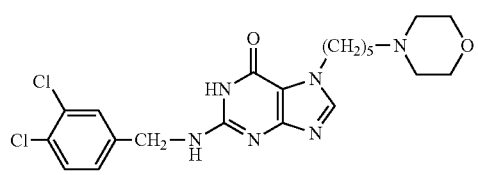

332E

|  |  | pol III inhibitors (see structures) | | | Antibiotics | | |
|---|---|---|---|---|---|---|---|
|  | Micromyx | | | | | | |
| Organism* | Number | 179E | 315C | 332E | Van** | Met** | Clin** |
| Gram positives: | | | | | | | |
| L. casei | 1722 | 32 | 32 | >32 | >16 | >16 | 2 |
| L. acidophilus | 0681 | 32 | 16 | 8 | 2 | >16 | 4 |
| Bi. brevi | 3967 | >32 | >32 | 32 | 2 | >16 | 0.12 |
| Bi. longum | 3968 | >32 | >32 | >32 | 0.5 | 4 | ≤0.03 |
| E. lentum | 1274 | >32 | >32 | 32 | 2 | 0.5 | 0.12 |
| C. difficile | 3579 | 16 | 16 | 4 | 1 | 0.25 | 16 |
| C. difficile | 3580 | 4 | 8 | 4 | 1 | 0.5 | 8 |
| C. difficile | 3581 | 8 | 8 | 4 | 1 | 1 | >16 |
| C. difficile | 3582 | 16 | >32 | 16 | 0.25 | 0.25 | 0.5 |
| C. difficile | 3584 | 4 | 8 | 2 | 0.5 | 0.5 | 8 |
| C. difficile | 3585 | 16 | 16 | 4 | 0.5 | 0.5 | 8 |
| C. difficile | 3586 | 4 | 8 | 2 | 0.5 | 0.5 | 8 |
| C. difficile | 3587 | 8 | 8 | 4 | 1 | 1 | 8 |
| C. difficile | 3588 | 1 | 4 | 1 | 2 | 0.5 | 8 |
| C. difficile | 3589 | 16 | 16 | 4 | 0.5 | 1 | >16 |
| C. difficile | 3590 | 8 | 8 | 4 | 1 | 0.5 | 8 |
| C. difficile | 3591 | 8 | 8 | 4 | 2 | 0.5 | 8 |
| C. difficile | 3593 | 16 | 16 | 4 | 0.5 | 0.5 | 8 |
| C. difficile | 3594 | 4 | 8 | 4 | 1 | 1 | >16 |
| C. difficile | 3595 | 4 | 8 | 4 | 1 | 1 | >16 |
| C. difficile | 1209 | 16 | 16 | 4 | 1 | 0.5 | 4 |
| C. difficile | 4381† | 4 | 8 | 2 | 1 | 0.5 | 4 |
| Gram negative: | | | | | | | |
| Ba. fragilis | 0123† | >32 | >32 | >32 | >16 | 1 | 1 |

*L., Lactobacillus; Bi, Bifidobacterium; E, Eubacterium; C, Clostridium; Ba, Bacillus.
†ATCC strains.
**Van, vancomycin; Met, metronidazole; Clin, clindamycin Testing of other analogs of formula I (see structures below) confirmed the anti C. diff. activity of these compounds (Table 2).

TABLE 2

MICs (μg/ml) of DCB compounds and comparators against C. diff. strains.

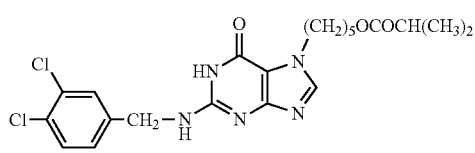

332E

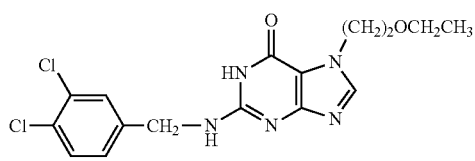

325E

TABLE 2-continued

359E

|  |  | DCB compounds | | | comparators | |
|---|---|---|---|---|---|---|
|  | Micromyx | | | | Vanco- | Metroni- |
| Organism* | Number | 332E | 325E | 359E | mycin | dazole |
| C. diff. | 3579 | 4 | 2 | 2 | 1 | 0.5 |
| " | 3580 | 4 | 2 | 2 | 1 | 0.5 |
| " | 3581 | 2 | 1 | 2 | 4 | 0.5 |
| " | 3582† | 4 | 2 | 2 | 2 | 0.5 |
| B. fragilis | 0123† | >32 | >32 | >32 | 32 | 0.5 |

*Clinical isolates, except:
†(ATCC strains)

A more detailed screen of isosteric analogs of compound 359E (see structures below) revealed that 359E had the best profile, i.e., high potency against C. diff. strains and low potency against other Gram-positive anaerobes (Table 3).

TABLE 3

MICs (μg/ml) of isosteres of 359E and ccomparator against *C. diff.* strains.

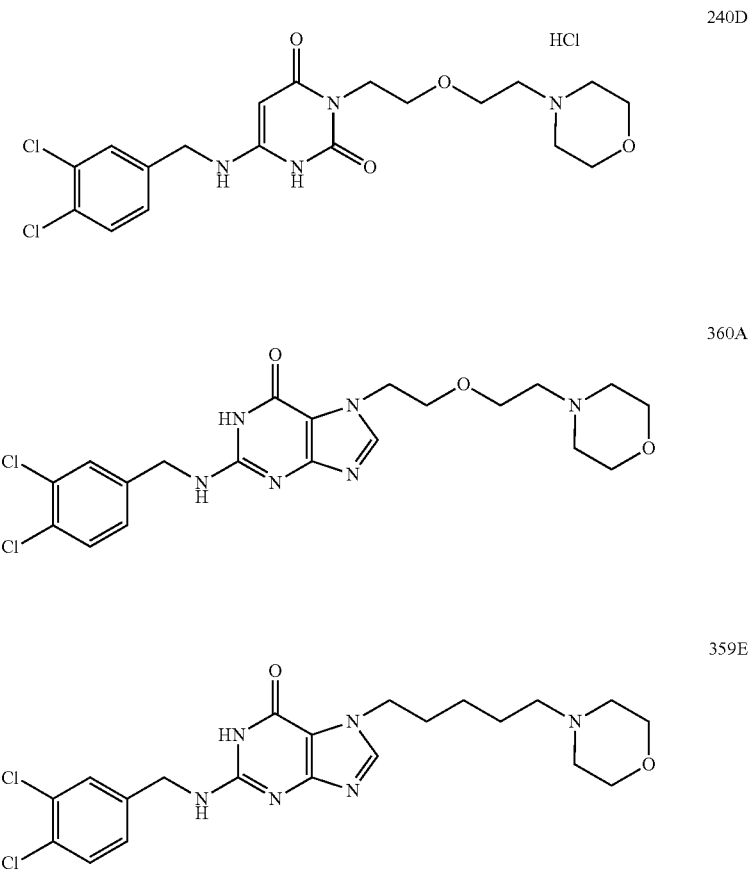

| Organism* | Strain no. | DCB compounds | | | comparator |
|---|---|---|---|---|---|
| | | 240D | 360A | 359E | Metronidazole |
| Gram-positives: | | | | | |
| L. casei | 1722† | >32 | >32 | 16 | >32 |
| L. acidophilus | 0681 | 16 | 16 | 2 | >32 |
| Bi. Breve | 3967† | >32 | >32 | >32 | 4 |
| Bi. Longum | 3968† | >32 | >32 | >32 | 4 |
| Eu. Lentum | 1274† | >32 | >32 | >32 | 0.5 |
| C. diff. | 3580 | 32 | 16 | 4 | 1 |
| " | 3581 | 8 | 8 | 2 | 1 |
| " | 3582 | 32 | 16 | 8 | 0.5 |
| " | 3584 | 8 | 4 | 2 | 0.5 |
| " | 3585 | 16 | 16 | 4 | 1 |
| " | 3586 | 8 | 4 | 2 | 0.12 |
| " | 3587 | 16 | 8 | 4 | 1 |
| " | 3588 | 2 | 1 | 0.5 | 0.5 |
| " | 3589 | 16 | 16 | 4 | 2 |
| " | 4381† | 8 | 8 | 2 | 0.5 |
| Gram-negative (control): | | | | | |
| B. fragilis | 0123† | >32 | >32 | >32 | 0.5 |

*L., *Lactobacillus*; Bi, *Bifidobacterium*; E, *Eubacterium*; C, *Clostridium*; Ba, *Bacillus*.
†ATCC strains Finally, synthesis and testing of close analogs of compound 359E revealed that the corresponding propyl (compound 363A) and butyl analogs (compound 258D) and the methyl analog (compound 362C) were similar in potency to 359E, but the ethyl analog (compound 362E) had preferred activity against *C. diff.* strains (Table 4).

TABLE 4

MICs (μg/ml) of compounds and comparators against *C. diff.* strains.

| | Compound | | | | | comparators | metroni- |
|---|---|---|---|---|---|---|---|
| Strain no. | 258D | 359E | 362C | 363C | 362A | vancomycin | dazole |
| 19265 | 4 | 8 | 8 | 8 | 2 | 1 | 0.5 |
| 19273 | 8 | 8 | 8 | 4 | 4 | 1 | 0.25 |
| 19281 | 4 | 8 | 8 | 8 | 2 | 1 | 0.5 |
| 18285 | 8 | 8 | 8 | 8 | 4 | 1 | 2 |
| 19291 | 4 | 4 | 4 | 4 | 2 | 1 | 0.5 |
| 19369 | 16 | 8 | 8 | 8 | 8 | 1 | 0.5 |
| 19382 | 4 | 2 | 2 | 2 | 2 | 4 | 0.5 |
| 19540 | 4 | 4 | 2 | 4 | 2 | 1 | 4 |
| 19580 | 2 | 2 | 2 | 2 | 2 | 4 | 2 |
| 19680 | 4 | 8 | 8 | 8 | 2 | 1 | 4 |
| 19681 | 4 | 8 | 8 | 4 | 2 | 2 | 1 |
| 19683 | 8 | 8 | 8 | 8 | 4 | 8 | 2 |
| 19687 | 8 | 8 | 8 | 8 | 4 | 1 | 4 |
| 20066 | 8 | 8 | 8 | 8 | 4 | 4 | 4 |
| 20152 | 16 | 8 | 8 | 8 | 8 | 1 | 1 |
| 20307 | 4 | 8 | 4 | 2 | 2 | 2 | 0.5 |
| 20494 | 4 | 8 | 8 | 8 | 2 | 4 | 1 |
| 20680 | 4 | 8 | 4 | 8 | 2 | 1 | 4 |
| 20934 | 4 | 2 | 2 | 2 | 1 | 4 | 1 |
| 21099 | 2 | 8 | 8 | 8 | 2 | 2 | 2 |

Example 3

Protection of Hamsters from *C. diff.*-Associated Infection

The clindamycin-induced *C. diff.* infection model in Syrian golden hamsters serves to demonstrate the efficacy of the test compounds against experimental *C. diff.*-associated diarrhea (CDAD) in vivo. Compound 359E protected hamsters from lethal infection with *C. diff.* (see Table 5).

Compound 359E was given orally as a suspension in 1% carboxymethylcellulose to Syrian Golden hamsters, pretreated subcutaneously with clindamycin and infected orally with *C. diff.* (ATCC43255) as described in Table 5. The response to a twice daily regimen of oral 359E and comparison with the efficacy of oral vancomycin are presented in Table 5.

TABLE 5

*C. diff.* infection model in Syrian golden hamsters*

| Group# n = 6 | Treatment, PO, bid, for 3 days | Survivors at | | | | | % Survivors at 120 hr |
|---|---|---|---|---|---|---|---|
| | | 24 hr | 48 hr | 66 hr | 72 hr | 96 hr | |
| 1 | neg. control, no-treatment | 6 | 4 | 0 | | | 0 |
| 2 | vancomycin HCl in water, 50 mg/kg bid for 3 days | 6 | 6 | 6 | 6 | 6 | 100 |
| 3 | 359E, in 1% CMC in water, 50 mg/kg bid for 3 days | 6 | 6 | 6 | 6 | 6 | 100 |
| 4 | 359E, in 1% CMC in water, 25 mg/kg bid for 3 days | 6 | 6 | 6 | 6 | 6 | 100 |

*All animals were pretreated with clindamycin hydrochloride (15 mg/kg, SC) one day before oral infection with ca. $10^6$ CFU *C. diff.*

Other Embodiments

A number of embodiments of the invention have been described. Nevertheless, it will be understood that various modifications can be made without departing from the spirit and scope of the invention. Accordingly, other embodiments are within the scope of the following claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other embodiments are in the claims.

What is claimed is:

1. A compound having the formula:

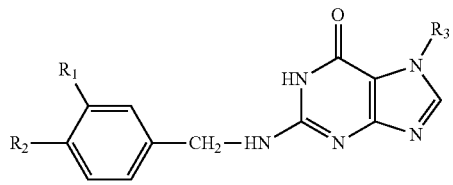

I wherein $R^1$ and $R^2$ are, independently, H, halo, $C_{1-6}$ haloalkyl, or $C_{1-6}$ haloalkoxy;
  wherein $R^3$ is $(CH_2)_m$—B;
in which B is H, substituted or unsubstituted $C_{3-8}$ cycloalkyl, substituted or unsubstituted $C_{2-8}$ heterocyclyl or $C_{1-10}$ heteroaryl, or $OR^{12}$, in which $R^{12}$ is substituted $C_{1-6}$ alkyl, wherein the substituent is a heterocyclyl; and m is 1-3;
  or an optical isomer thereof, or a pharmaceutically acceptable salt thereof.

2. The compound of claim 1, $R^1$ and $R^2$ are, independently H, halo, trihalomethyl, trifluoroethyl, or trihalomethoxy.

3. The compound of claim 1, wherein $R^1$ and $R^2$ are chloro.

4. The compound of claim 1, wherein $R^3$ is 2-(N-morpholinyl)ethyl, 3-(N-morpholinyl)propyl, 2-[(N-morpholinyl)ethoxy]ethyl, 2-[(N-morpholinyl)-methyl]cyclobutylmethyl, or 2-[(N-morpholinyl)methyl]cyclopentylmethyl.

5. The compound of claim 1, wherein $R^1$ and $R^2$ are selected, independently, from the group consisting of Cl, Br, I, $CF_3$, $OCF_3$, $CF_2CF_3$, and $CH_2CF_3$.

6. The compound of claim 1, having the formula:

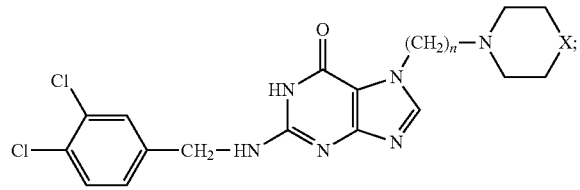

n = 2 or 3; X = $CH_2$, NH, O

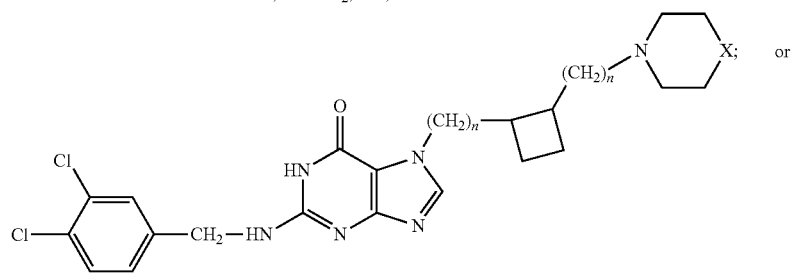

n = 1 or 2; X = $CH_2$, NH, O

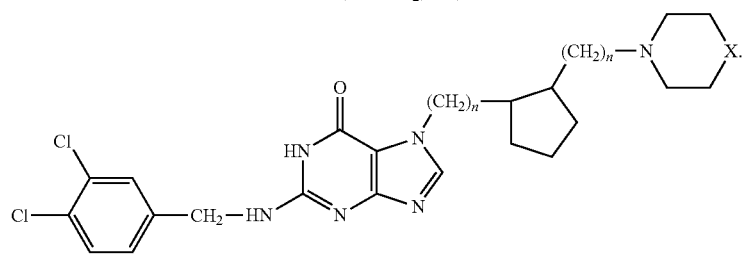

n = 1 or 2; X = $CH_2$, NH, O

7. The compound of claim 1, selected from the group consisting of:
  7-[2-(N-morpholinyl)ethyl]-2-(3,4-dichlorobenzylamino)-6-oxopurine (cpd 362E);
  7-[2-(N-morpholinyl)ethyl]-2-(3,4-dichlorobenzylamino)-6-oxopurine hydrochloride;
  7-[3-(N-morpholinyl)propyl]-2-(3,4-dichlorobenzylamino)-6-oxopurine (cpd 363A);
  7-[3-(N-morpholinyl)propyl]-2-(3,4-dichlorobenzylamino)-6-oxopurine hydrochloride;
  7-[2-(N-morpholinyl)ethoxyethyl]-2-(3,4-dichlorobenzylamino)-6-oxopurine;
  7-[2-(N-piperidinyl)ethoxyethyl]-2-(3,4-dichlorobenzylamino)-6-oxopurine;
  7-[2-(N-azetidinyl)ethoxyethyl]-2-(3,4-dichlorobenzylamino)-6-oxopurine;
  7-[2-(N-pyrrolidinyl)ethoxyethyl]-2-(3,4-dichlorobenzylamino)-6-oxopurine;
  7-{2-[(N-morpholinyl)methyl]cyclobutylmethyl}-2-(3,4-dichlorobenzylamino)-6-oxopurine;
  7-{2-[(N-morpholinyl)methyl]cyclobutylmethyl}-2-(3,4-dichlorobenzylamino)-6-oxopurine hydrochloride;
  7-{2-[(N-morpholinyl)methyl]cyclopentylmethyl}-2-(3,4-dichlorobenzylamino)-6-oxopurine hydrochloride;
  7-{2-[(N-morpholinyl)methyl]cyclobutylmethyl}-2-(3,4-dichlorobenzylamino)-6-oxopurine;
  7-{2-[(N-piperidinyl)methyl]cyclobutylmethyl}-2-(3,4-dichlorobenzylamino)-6-oxopurine; and
  7-{2-[(N-piperidinyl)methyl]cyclopentylmethyl}-2-(3,4-dichlorobenzylamino)-6-oxopurine.

8. A pharmaceutical composition comprising a compound of claim 1 and a pharmaceutically acceptable excipient.

9. A method of inhibiting growth of *Clostridium difficile* in vitro, the method comprising contacting, in an appropriate culture medium in the absence of oxygen, *Clostridium difficile* with an effective amount of a compound having the formula:

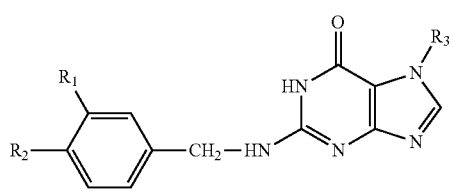

wherein $R^1$ and $R^2$ are, independently, H, halo, $C_{1-6}$ haloalkyl, or $C_{1-6}$ haloalkoxy;
wherein $R^3$ is $(CH_2)_m$—B;
in which B is substituted or unsubstituted $C_{3-8}$ cycloalkyl, substituted or unsubstituted $C_{2-8}$ heterocyclyl or $C_{1-10}$ heteroaryl, or $OR^{12}$, in which $R^{12}$ is substituted $C_{1-6}$ alkyl, wherein the substituent is a heterocyclyl; and m is 1-3;

or an optical isomer thereof, or a pharmaceutically acceptable salt thereof.

10. The method of claim 9, wherein R$^1$ and R$^2$ are chloro.

11. The method of claim 9, wherein said compound is selected from the group consisting of:

7-[2-(N-morpholinyl)ethyl]-2-(3,4-dichlorobenzylamino)-6-oxopurine (cod 362E);
7-[2-(N-morpholinyl)ethyl]-2-(3,4-dichlorobenzylamino)-6-oxopurine hydrochloride;
7-[3-(N-morpholinyl)propyl]-2-(3,4-dichlorobenzylamino)-6-oxopurine (cod 363A);
7-[3-(N-morpholinyl)propyl]-2-(3,4-dichlorobenzylamino)-6-oxopurine hydrochloride;
7-[2-(N-morpholinyl)ethoxyethyl]-2-(3,4-dichlorobenzylamino)-6-oxopurine;
7-[2-(N-piperidinyl)ethoxyethyl]-2-(3,4-dichlorobenzylamino)-6-oxopurine;
7-[2-(N-azetidinyl)ethoxyethyl]-2-(3,4-dichlorobenzylamino)-6-oxopurine;
7-[2-(N-pyrrolidinyl)ethoxyethyl]-2-(3,4-dichlorobenzylamino)-6-oxopurine;
7-{2-[(N-morpholinyl)methyl]cyclobutylmethyl}-2,4-dichlorobenzylamino)-6-oxopurine,
7-{2-[(N-morpholinyl)methyl]cyclobutylmethyl}-2-(3,4-dichlorobenzylamino)-6-oxopurine hydrochloride;
7-{2-[(N-morpholinyl)methyl]cyclopentylmethyl}-2-(3,4-dichlorobenzylamino)-6-oxopurine hydrochloride;
7-{2-[(N-morpholinyl)methyl]cyclobutylmethyl}-2-(3,4-dichlorobenzylamino)-6-oxopurine;
7-{2-[(N-piperidinyl)methyl]cyclobutylmethyl}-2-(3,4-dichlorobenzylamino)-6-oxopurine; and
7-{2-[(N-piperidinyl)methyl]cyclopentylmethyl}-2-(3,4-dichlorobenzylamino)-6-oxopurine.

12. The compound of claim 1, wherein said compound is 7-[2-(N-morpholinyl)ethyl]-2-(3,4-dichlorobenzylamino)-6-oxopurine (cpd 362E) or 7-[2-(N-morpholinyl)ethyl]-2-(3,4-dichlorobenzylamino)-6-oxopurine hydrochloride.

13. The method of claim 9, wherein said compound is 7-[2-(N-morpholinyl)ethyl]-2-(3,4-dichlorobenzylamino)-6-oxopurine (cpd 362E) or 7-[2-(N-morpholinyl)ethyl]-2-(3,4-dichlorobenzylamino)-6-oxopurine hydrochloride.

* * * * *